(12) United States Patent
Cha

(10) Patent No.: US 11,234,646 B2
(45) Date of Patent: Feb. 1, 2022

(54) BODY COMPOSITION MEASUREMENT USING CLAMP ELECTRODES

(71) Applicant: InBody Co., Ltd., Seoul (KR)

(72) Inventor: Ki Chul Cha, Seoul (KR)

(73) Assignee: InBody Co., Ltd., Seoul (KR)

( * ) Notice: Subject to any disclaimer, the term of this patent is extended or adjusted under 35 U.S.C. 154(b) by 688 days.

(21) Appl. No.: 15/719,363

(22) Filed: Sep. 28, 2017

(65) Prior Publication Data

US 2018/0098735 A1 Apr. 12, 2018

(30) Foreign Application Priority Data

Oct. 6, 2016 (KR) .......................... 10-2016-0128841

(51) Int. Cl.
*A61B 5/00* (2006.01)
*A61B 5/0537* (2021.01)

(52) U.S. Cl.
CPC .......... *A61B 5/6838* (2013.01); *A61B 5/0537* (2013.01); *A61B 5/6823* (2013.01); *A61B 5/6842* (2013.01); *A61B 5/6824* (2013.01); *A61B 5/6828* (2013.01)

(58) Field of Classification Search
CPC ... A61B 5/6838; A61B 5/0537; A61B 5/6823; A61B 5/6842; A61B 5/6824; A61B 5/6828
See application file for complete search history.

(56) References Cited

U.S. PATENT DOCUMENTS

| 923,217 | A | 6/1909 | Tyrrell |
| 1,091,413 | A | 3/1914 | Wilkins |
| 4,612,936 | A | 9/1986 | Yamaguchi et al. |

(Continued)

FOREIGN PATENT DOCUMENTS

| CN | 201167950 Y | 12/2008 |
| CN | 202526171 U | 11/2012 |

(Continued)

OTHER PUBLICATIONS

Hamaguchi T; Karo H; Oku S; Japanese Patent JP 2008228994—'Electrode Clip'; EPO [Retreived and translated on Jun. 24, 2020]—(Year: 2008).*

(Continued)

*Primary Examiner* — Eun Hwa Kim
*Assistant Examiner* — Adam Z Minchella
(74) *Attorney, Agent, or Firm* — K&L Gates LLP

(57) ABSTRACT

A clamp electrode apparatus comprises first and second clamps which are mechanically connected to form a single integrated device and arranged side by side such that a first edge of the first clamp faces a second edge of the second clamp. A channel is defined between the first and second edges for aligning a visible mark feature of a limb, such as a malleolus or ulnar head, within the opening or channel when the first and second clamps clamp the limb. When the limb is clamped with the clamp electrode apparatus multiple times, the visible mark feature can be aligned with reference to the channel. Thus, electrodes attached to the clamps contact generally the same locations even if the clamp electrode apparatus is removed after each measurement and is not kept on the limb throughout the multiple measurements.

10 Claims, 13 Drawing Sheets

(56) References Cited

U.S. PATENT DOCUMENTS

| | | | |
|---|---|---|---|
| 5,720,296 | A | 2/1998 | Cha |
| 7,203,536 | B2 | 4/2007 | Masuo |
| 7,628,761 | B2 | 12/2009 | Gozani et al. |
| 8,868,175 | B2 | 10/2014 | Arad (Abboud) |
| 8,965,497 | B2 | 2/2015 | Tournefier et al. |
| 9,107,586 | B2 | 8/2015 | Tran |
| 9,591,987 | B1* | 3/2017 | Liedtke ............... A61B 5/0537 |
| 2003/0073925 | A1* | 4/2003 | Komatsu ............ A61B 5/7435 |
| | | | 600/547 |
| 2004/0059242 | A1 | 3/2004 | Masuo et al. |
| 2005/0209528 | A1* | 9/2005 | Sato ..................... A61B 5/0537 |
| | | | 600/547 |
| 2005/0215933 | A1 | 9/2005 | Stearns et al. |
| 2008/0306401 | A1* | 12/2008 | Okura .................. A61B 5/0537 |
| | | | 600/547 |
| 2009/0043222 | A1 | 2/2009 | Chetham |
| 2010/0152605 | A1 | 6/2010 | Ward |
| 2011/0204615 | A1 | 8/2011 | Roberts |
| 2013/0023751 | A1 | 1/2013 | Lichtenstein et al. |
| 2013/0197340 | A1 | 8/2013 | Sanders et al. |
| 2013/0303935 | A1* | 11/2013 | Uchiyama ............ A61B 5/0537 |
| | | | 600/547 |
| 2014/0200423 | A1 | 7/2014 | Eisen et al. |
| 2015/0374256 | A1 | 12/2015 | Skrabal |
| 2016/0296171 | A1* | 10/2016 | Drori ................... A61B 5/0402 |

FOREIGN PATENT DOCUMENTS

| | | | |
|---|---|---|---|
| CN | 203195682 U | | 9/2013 |
| CN | 204218903 U | | 3/2015 |
| DE | 9112497 U1 | | 1/1992 |
| JP | 11-332843 A | | 12/1999 |
| JP | 2000-139868 A | | 5/2000 |
| JP | 2003-299629 A | | 10/2003 |
| JP | 2008-061825 A | | 3/2008 |
| JP | 2008-168075 A | | 7/2008 |
| JP | 2008-228994 A | | 10/2008 |
| JP | 2008228994 | * | 10/2008 ............... A61B 5/05 |
| JP | 2009-531157 A | | 9/2009 |
| JP | 2010-069225 A | | 4/2010 |
| JP | 5050595 B2 | | 10/2012 |
| KR | 2003-0081340 A | | 10/2003 |

OTHER PUBLICATIONS

Scheltinga et al., "Alterations in Body Fluid Content Can Be Detected by Bioelectrical Impedance Analysis", Journal of Surgical Research, 1991, vol. 50, pp. 461-468.

RJL Systems, "Eight Electrode Segmental BIA", Jun. 4, 2010, 18 pages.

* cited by examiner

BODY COMPOSITION MEASUREMENT USING CLAMP ELECTRODES

BACKGROUND

Field

The present disclosure relates to a body composition measurement.

Discussion of Related Technology

Generally, body composition is used to describe what percentage of a human body is water, fat, bone, muscle, or the like. Analysis of body composition provides benefits. For example, in physical fitness, body composition information of a person can be used for establishing a personalized exercise plan. For overweight people, body composition information can provide a visual warning to lead to formation of a personal diet goal. Physicians can use body composition information to treat a patient. Bioelectrical impedance analysis is one of many ways to estimate body composition. The above applications of body composition information generally require accurate analysis of body composition, which depends on accurate measurement of electrical impedance of body portions.

SUMMARY

One aspect of the invention provides a clamp electrode apparatus, which may comprise:
- a first clamp comprising a first upper clamp body and a first lower clamp body operably connected to each other such that the first upper and lower clamp bodies are movable relative to each other for clamping a first portion of a limb of a subject between the first upper and lower clamp bodies;
- a second clamp comprising a second upper clamp body and a second lower clamp body operably connected to each other such that the second upper and lower clamp bodies are movable relative to each other for clamping a second portion of the limb adjacent the first portion between the second upper and lower clamp bodies;
- the first and second clamps mechanically connected to form a single integrated device and arranged side by side such that a first edge of the first upper clamp body faces a second edge of the second upper clamp body and an opening or channel is defined between the first edge and the second edge for aligning a visible mark feature of the limb within the opening or channel when the first and second clamps clamp the limb;
- a first electrode disposed on an inner surface of the first or second clamp and configured to contact a first surface of the limb when the limb is clamped with both the first and second clamps; and
- a second electrode electrically independent of the first electrode and disposed on an inner surface of the first or second clamp and configured to contact a second surface of the limb other than the first surface when the limb is clamped with both the first and second clamps, wherein when the limb of the same subject is clamped with the first and second clamps multiple times, the visible mark feature can be aligned with reference to the opening or channel between the first and second edges such that the first electrode contacts the same first surface of the limb and the second electrode contacts the same second surface of the limb, which enables multiple measurements of the same subject with electrical contacts generally at the same locations of the limb even if the clamp electrode apparatus is removed from the limb after each measurement and is not kept on the limb throughout the multiple measurements.

In the foregoing apparatus, the first upper clamp body and the upper lower clamp body may be independently movable relative to each other, wherein the first lower clamp body and the second lower clamp body may be independently movable relative to each other. The first upper clamp body and the upper lower clamp body may be independently movable relative to each other, wherein the first lower clamp body and the second lower clamp body may be integrated such that they are not movable relative to each other.

Still in the foregoing apparatus, the first electrode may be disposed on the first clamp and the second electrode is disposed on the second clamp. The first electrode may be disposed on the first clamp, and the second electrode may be disposed on the second clamp, wherein one of the first and second clamps is located at a more proximal location than the other of the first and second clamps along a longitudinal direction when the limb is clamped with the first and second clamps.

Yet in the foregoing apparatus, the first upper and lower clamp bodies may be hingedly connected with each other such that the first upper clamp body is configured to hingedly rotate about a first hinge axis, wherein the second upper and lower clamp bodies are hingedly connected with each other such that the second upper clamp body is configured to hingedly rotate about a second hinge axis which is the same as the first hinge axis, generally parallel to the first hinge axis, or substantially non-parallel to the first hinge axis.

Further in the foregoing apparatus, the apparatus may further comprise:
- the first and second electrodes disposed on the inner surface of the first upper clamp body and the second upper clamp body;
- a third electrode disposed on the inner surface of the first lower clamp body and facing the first electrode, wherein, when the limb is clamped with the apparatus, the third electrode is configured to contact a third surface of the limb located at the same distance of the first surface from the visible mark feature when measured along the longitudinal direction of the limb; and
- a fourth electrode disposed on the inner surface of the second lower clamp body and facing the second electrode, the fourth electrode is configured to contact a fourth surface of the limb located at the same distance of the second surface from the visible mark feature when measured along the longitudinal direction of the limb,
wherein when the limb of the same subject is clamped with the first and second clamps multiple times, the visible mark feature can be aligned with reference to the opening or channel between the first and second edges such that the third electrode contacts the same third surface of the limb and the fourth electrode contacts the same fourth surface of the limb, which enables multiple measurements of the same subject with electrical contacts generally at the same locations of the limb even if the clamp electrode apparatus is removed from the limb after each measurement and is not kept on the limb throughout the multiple measurements.

Another aspect of the invention provides a measurement system, which may comprise:

a first electrode apparatus being the above clamp electrode apparatus and mountable on a first one of limbs of a subject, a second electrode apparatus comprising a fifth electrode and a sixth electrode and mountable on a second one of the limbs of the same subject;

a current source circuit;

a voltage measurement circuit;

first, second, third, fourth, fifth and sixth terminals configured to be connected to the first, second, third, fourth, fifth and sixth electrodes, respectively; and at least one switching circuit configured to connect each of the first, second, third, fourth, fifth and sixth terminals to either the current source circuit or the voltage measurement circuit, wherein the at least one switching circuit is configured to switch the connection of each of the first and second terminals to the current source circuit and further configured to switch the connection of each of the third and fourth terminals to the voltage measurement circuit such that:

in a first measurement, the first and fifth terminals are connected to the current source and the third and sixth terminals are connected to the voltage measurement circuit, and in a second measurement immediately subsequent to the first measurement, the second and fifth terminals are connected to the current source circuit and the fourth and the sixth terminals are connected to the voltage measurement circuit while the clamp electrode apparatus maintains clamping the first limb, wherein the at least one circuit configured to connect the fifth electrode to the current source circuit and further configured to connect the sixth electrode to the voltage measurement circuit both in the first measurement and the second measurement.

In the foregoing measurement system, the clamp electrode apparatus is referred to as a first clamp electrode apparatus, wherein the second electrode apparatus may be a second clamp electrode apparatus comprising the same features as the first clamp electrode apparatus.

Still in the foregoing measurement system, the clamp electrode apparatus is referred to as a first clamp electrode apparatus, wherein the second electrode apparatus may be a second clamp electrode apparatus which comprises:

a single clamp comprising an upper clamp body and a lower clamp body operably connected to each other such that the upper and lower clamp bodies are movable relative to each other for clamping a portion of the second limb between the upper and lower clamp bodies;

an extension coupled to an edge of one of the upper and lower clamp bodies;

an opening or channel defined between the extension and the edge for aligning a visible mark feature of the second limb within the opening or channel when the single clamp clamps the second limb;

the fifth and sixth electrodes, each of which is disposed on an inner surface of one of the upper and lower clamp bodies, the fifth electrode configured to contact a fifth surface of the second limb when the second limb is clamped with the single clamp, the sixth electrode electrically independent of the fifth electrode and configured to contact a sixth surface of the second limb other than the fifth surface when the second limb is clamped with the single clamp, wherein when the second limb of the same subject is clamped with the single clamp multiple times, the visible mark feature can be aligned with reference to the opening or channel between the edge and the extension of the single clamp such that the third electrode contact the same third surface of the other limb and the fourth electrode contacts the same fourth surface of the second limb, which enables multiple measurements of the subject with electrical contacts generally at the same locations of the second limb even if the second clamp electrode apparatus is removed from the second limb after each measurement and is not kept on the second limb throughout the multiple measurements.

Still another aspect of the invention provides a method of electrical measurements. The method may comprise:

providing the above measurement system;

clamping a first limb of a subject with the first clamp electrode apparatus such that a first visible mark feature of the first limb is positioned within the opening or channel of the first clamp electrode apparatus and such that the first, second, third and fourth electrodes contact first, second, third and fourth surfaces of the first limb;

clamping a second limb of the subject with the second clamp electrode apparatus such that a second visible mark feature of the second limb is positioned within the opening or channel of the second clamp electrode apparatus and such that the fifth and sixth electrodes contact fifth and sixth surfaces of the second limb;

electrically connecting the first, second, third, fourth, fifth and sixth electrodes to the first, second, third, fourth, fifth and sixth terminals;

conducting the first measurement while the first and fifth terminals are connected to the current source circuit, the third and sixth terminals are connected to the voltage measurement circuit, wherein the first measurement is made between the third electrode and the sixth electrode to acquire a first voltage drop between the third and sixth electrodes;

while maintaining clamping of the first limb with the first clamp electrode apparatus and further maintaining clamping of the second limb with the second clamp electrode apparatus, switching electrical connections of the first, second, third and fourth terminals such that the first and third terminals are disconnected from the current source circuit and the voltage measurement circuit, respectively, and the second and fourth terminals are connected to the current source circuit and the voltage measurement circuit, respectively, while maintaining the fifth terminal's connection to the current source circuit and the sixth terminal's connection to the voltage measurement circuit; and conducting the second measurement while the second and sixth terminals are connected to the current source circuit and the fourth and sixth terminals are connected to the voltage measurement circuit, wherein the second measurement is made between the fourth electrode and the sixth electrode to acquire a second voltage drop between the fourth and sixth electrodes.

The foregoing method may further comprise processing the first and second voltage drops to obtain a value representing impedance of a section of the first limb between the first and second electrodes. The foregoing method may further comprise calculating a value representing impedance of a body section comprising an arm, a trunk and a leg using the first and second voltage drops. The foregoing method may further comprise processing the first and second voltage drops with a formula or a lookup table to assess the body composition of the subject.

In the foregoing method, the first limb may be a leg, the second limb may be an arm, the first visible mark feature is a malleolus and the second visible mark feature is an ulnar head. The first limb may be an arm, the second limb may be a leg, the first visible mark feature is an ulnar head and the second visible mark feature is a malleolus. The first limb may be a leg which comprising an ankle section between the first and second electrodes and the first visible mark feature is a malleolus, wherein the method may further comprise: processing the first and second voltage drops to obtain a value representing body water amount in the ankle section; and determining if the obtained value is greater than a predetermined value; and when determined that the obtained value is greater than a predetermined value, determining that the subject has edema.

The foregoing method may further comprise:
  unclamping the first and second limbs of the subject; and
  after a predetermined time period, repeating the electrical measurement, wherein repeating comprises:
    re-clamping the first limb of the subject with the first clamp electrode apparatus such that the first visible mark feature of the first limb is positioned within the opening or channel of the first clamp electrode apparatus and such that the first, second, third and fourth electrodes contact again the first, second, third and fourth surfaces of the first limb;
    re-clamping the second limb of the subject with the second clamp electrode apparatus such that the second visible mark feature of the second limb is positioned within the opening or channel of the second clamp electrode apparatus and such that the fifth and sixth electrodes contact again the fifth and sixth surfaces of the second limb;
    electrically connecting the first, second, third, fourth, fifth and sixth electrodes to the first, second, third, fourth, fifth and sixth terminals;
    conducting a third measurement while the first and fifth terminals are connected to the current source circuit, the third and sixth terminals are connected to the voltage measurement circuit, wherein the first measurement is made between the third electrode and the sixth electrode to acquire a third voltage drop between the third and sixth electrodes;
    while maintaining clamping of the first limb with the first clamp electrode apparatus and further maintaining clamping of the second limb with the second clamp electrode apparatus, switching electrical connections of the first, second, third and fourth terminals such that the first and third terminals are disconnected from the current source circuit and the voltage measurement circuit, respectively, and the second and fourth terminals are connected to the current source circuit and the voltage measurement circuit, respectively, while maintaining the fifth terminal's connection to the current source circuit and the sixth terminal's connection to the voltage measurement circuit, and
    conducting a fourth measurement while the second and sixth terminals are connected to the current source circuit and the fourth and sixth terminals are connected to the voltage measurement circuit, wherein the second measurement is made between the fourth electrode and the sixth electrode to acquire a fourth voltage drop between the fourth and sixth electrodes.

The foregoing method may further comprise: processing the first, second, third and fourth voltage drops to identify changes of body composition of the subject. The foregoing method may further comprise: processing the first, second, third and fourth voltage drops to obtain a value representing difference between water amounts in a section of the first limb at different measuring times; determining if the obtained value is greater than the predetermined value; and when determined that the obtained value is greater than a predetermined value, determining that the subject has edema.

A further aspect of the invention provides a measurement system, which may comprise:
  the above clamp electrode apparatus;
  a second electrode apparatus comprising a third electrode and a fourth electrode;
  a current source circuit;
  a voltage measurement circuit;
  first, second, third and fourth terminals configured to be connected to the first, second, third and fourth electrodes, respectively; and
  at least one switching circuit configured to connect each of the first, second, third and fourth terminals to either the current source circuit or the voltage measurement circuit, the at least one switching circuit configured to switch electrical connections of the first terminal and the second terminal to the current source circuit and the voltage measurement circuit such that in a first measurement the first terminal is connected to the current source and the second terminal is connected to the voltage measurement circuit and in a second measurement immediately subsequent to the first measurement the first terminal is connected to the voltage measurement circuit and the second terminal is connected to the current source circuit while the clamp electrode apparatus clamps the limb, the at least one circuit configured to connect the third electrode to the current source circuit and further configured to connect the fourth electrode to the voltage measurement circuit both in the first measurement and the second measurement.

In the foregoing measurement system, the at least one circuit may be configured to switch electrical connections of the third terminal and the fourth terminal to the current source circuit and the voltage measurement circuit such that in a third measurement the third terminal is connected to the current source and the second terminal is connected to the voltage measurement circuit and in a fourth measurement immediately subsequent to the third measurement the third terminal is connected to the voltage measurement circuit and the fourth terminal is connected to the current source circuit while the third and fourth electrodes contact another limb. The clamp electrode apparatus is referred to as a first clamp electrode apparatus, wherein the electrode apparatus may be a second clamp electrode apparatus comprising the same features as the first clamp electrode apparatus except the second clamp electrode apparatus comprises the third and fourth electrodes.

Still in the foregoing measurement system, the clamp electrode apparatus is referred to as a first clamp electrode apparatus, wherein the second electrode apparatus may be a second clamp electrode apparatus which comprises:
  a single clamp comprising an upper clamp body and a lower clamp body operably connected to each other such that the upper and lower clamp bodies are movable relative to each other for clamping a portion of another limb of a subject between the upper and lower clamp bodies;

an extension coupled to an edge of one of the upper and lower clamp bodies;

an opening or channel defined between the extension and the edge for aligning a visible mark feature of the other limb within the opening or channel when the single clamp clamps the other limb;

the third and fourth electrodes, each of which is disposed on an inner surface of one of the upper and lower clamp bodies, the third electrode configured to contact a third surface of the other limb when the other limb is clamped with the single clamp, the fourth electrode electrically independent of the third electrode and configured to contact a fourth surface of the other limb other than the third surface when the other limb is clamped with the single clamp, wherein when the other limb of the same subject is clamped with the single clamp multiple times, the visible mark feature can be aligned with reference to the opening or channel between the edge and the extension of the single clamp such that the third electrode contacts the same third surface of the other limb and the fourth electrode contacts the same fourth surface of the other limb, which enables multiple measurements of the subject with electrical contacts generally at the same locations of the other limb even if the second clamp electrode apparatus is removed from the other limb after each measurement and is not kept on the other limb throughout the multiple measurements.

Another further aspect of the invention provides a method of electrical measurements, which may comprise:

providing the above measurement system;

clamping an ankle portion of a first subject with the first clamp electrode apparatus such that the ankle portion is aligned with the first clamp electrode apparatus in which the malleolus of the ankle portion is positioned within the opening or channel of the first clamp electrode apparatus;

clamping a wrist portion of the first subject with the second clamp electrode apparatus such that the wrist portion is aligned with the second clamp electrode apparatus in which the ulnar head of the wrist portion is positioned within the opening or channel of the second clamp electrode apparatus;

electrically connecting the first electrode of the first clamp electrode apparatus to the first terminal, the second electrode of the first clamp electrode apparatus to the second terminal;

electrically connecting the third electrode of the second clamp electrode apparatus to the third terminal, the fourth electrode of the second clamp electrode apparatus to the fourth terminal;

conducting the first measurement while the first terminal is connected to the current source circuit, the second terminal is connected to the voltage measurement circuit, the third terminal is connected to the current source circuit, and the fourth terminal is connected to the voltage measurement circuit, wherein the first measurement is made between the second electrode and the fourth electrode to acquire a first voltage drop between the second and fourth electrodes;

while maintaining clamping of the ankle portion with the first clamp electrode apparatus and further maintaining clamping of the wrist portion with the second clamp electrode apparatus, switching electrical connections of the first and second terminals such that the first terminal is connected to the voltage measurement circuit, the second terminal is connected to the current source circuit while maintaining the third terminal's connection to the current source circuit and the fourth terminal's connection to the voltage measurement circuit; and conducting the second measurement while the first terminal is connected to the voltage measurement circuit, the second terminal is connected to the current source circuit, the third terminal is connected to the current source circuit, and the fourth terminal is connected to the voltage measurement circuit, wherein the second measurement is made between the first electrode and the fourth electrode to acquire a second voltage drop between the first and fourth electrodes.

The foregoing method may further comprise processing the first and second voltage drops to obtain a value representing impedance of the ankle section between the first and second electrodes. The foregoing method may further comprise calculating a value representing impedance of a body section comprising an arm, a trunk and a leg using the first and second voltage drops. The foregoing method may further comprise processing the first and second voltage drops with a formula or a lookup table to assess the body composition of the subject.

The foregoing method may further comprise:

unclamping the first and second limbs of the subject; and after a predetermined time period, repeating the electrical measurement, wherein repeating comprises:

re-clamping the ankle portion with the first clamp electrode apparatus such that the ankle portion is aligned with the first clamp electrode apparatus in which the malleolus of the ankle portion is positioned within the opening or channel of the first clamp electrode apparatus;

re-clamping the wrist portion with the second clamp electrode apparatus such that the wrist portion is aligned with the second clamp electrode apparatus in which the ulnar head of the wrist portion is positioned within the opening or channel of the second clamp electrode apparatus;

electrically connecting the first electrode of the first clamp electrode apparatus to the first terminal, the second electrode of the first clamp electrode apparatus to the second terminal;

electrically connecting the third electrode of the second clamp electrode apparatus to the third terminal, the fourth electrode of the second clamp electrode apparatus to the fourth terminal;

conducting a third measurement while the first terminal is connected to the current source circuit, the second terminal is connected to the voltage measurement circuit, the third terminal is connected to the current source circuit, and the fourth terminal is connected to the voltage measurement circuit, wherein the first measurement is made between the second electrode and the fourth electrode to acquire a third voltage drop between the second and fourth electrodes;

while maintaining clamping of the ankle portion with the first clamp electrode apparatus and further maintaining clamping of the wrist portion with the second clamp electrode apparatus, switching electrical connections of the first and second terminals such that the first terminal is connected to the voltage measurement circuit, the second terminal is connected to the current source circuit while maintaining the third terminal's connection to the current source circuit and the fourth terminal's connection to the voltage measurement circuit; and conducting a fourth measurement while the first terminal is connected to the voltage measurement circuit, the second terminal is connected to the current source circuit, the third terminal is connected to the current source circuit, and the fourth terminal is connected to the voltage measurement circuit, wherein the second measurement is made between the first electrode and the fourth electrode to acquire a fourth voltage drop between the first and fourth electrodes. The foregoing method may further comprise: processing the first, second, third and fourth voltage drops to identify changes of body composition of the subject.

BRIEF DESCRIPTION OF THE DRAWINGS

FIGS. 10 and 11 are schematic views of electric connections in the body composition measurement configuration shown in FIG. 4, wherein FIG. 10 shows a first measurement state and FIG. 11 shows a second measurement state.

FIGS. 18 and 19 are schematic views of electric connections in the body composition measurement configuration shown in FIG. 17, wherein FIG. 18 shows a first measurement state and FIG. 19 shows a second measurement state.

FIGS. 21 and 22 are schematic views of electric connections in the body composition measurement configuration shown in FIG. 20, wherein FIG. 21 shows a first measurement state and FIG. 22 shows a second measurement state.

DETAILED DESCRIPTION OF EMBODIMENTS

Embodiments of the invention will now be described with reference to the accompanying drawings. The terminology used in the description presented herein is not intended to be interpreted in any limited or restrictive manner, simply because it is being utilized in conjunction with a detailed description of certain specific embodiments of the invention.

Body Composition Analysis

A person's body composition can be analyzed by obtaining and processing impedances of body portions. Other information of the person such as height, weight, etc. may further be used for body composition analysis. In embodiments, a special formula is used for the body composition analysis. Impedances of body portions as well as with the height and weight are entered in the formula. Then, the formula provides analysis results, for example, in the form of numerical results. In some embodiments, gender and age of the person may also be used to provide more accurate analysis.

Impedance Measurement

Impedance of the body portions can be measured by electrical measurements. In embodiments, two current electrodes and two voltage electrodes are used to obtain impedance (or an electrical resistance value) for a body portion. For example, a current electrode pad and a voltage electrode pad are attached to or contacting a hand of a subject. Another current electrode and another voltage electrode are attached to or contacting a foot of the same subject. While supplying electric current between the hand and the foot via the two current electrodes, a voltage difference or voltage drop between the hand and the foot via the two voltage electrodes is measured. The amount of the applied current and the obtained voltage difference are processed to compute a value, which represents the impedance of a body portion extending from the hand to the foot via arm, trunk and leg.

Body Composition Measurement of Hospitalized Patients

Figure 1:
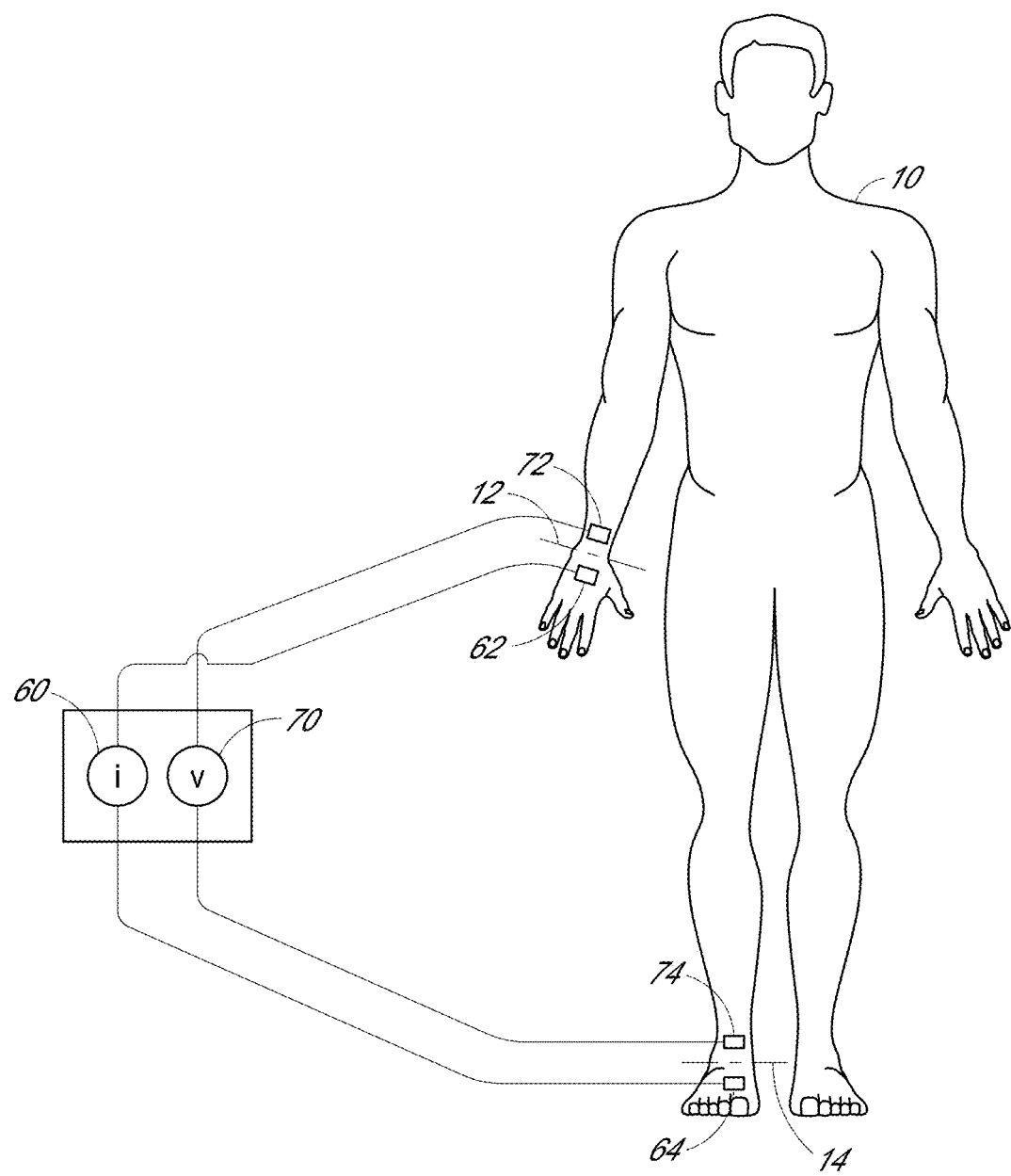
FIG. 1 is a schematic view illustrating a body composition measurement of a human body according to embodiments of the invention.
Figure 2:
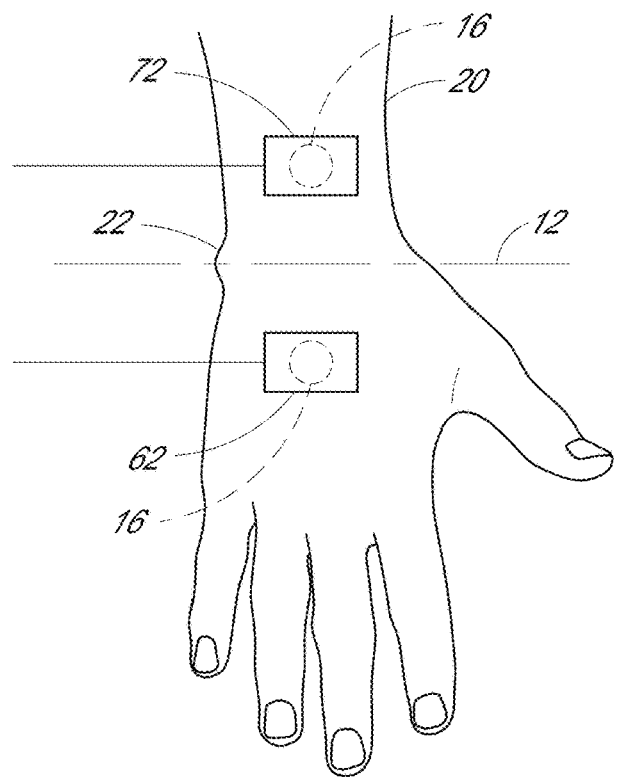
FIG. 2 is an enlarged view illustrating a wrist portion of an arm with electrode pads, which is shown in FIG. 1.
Figure 3:
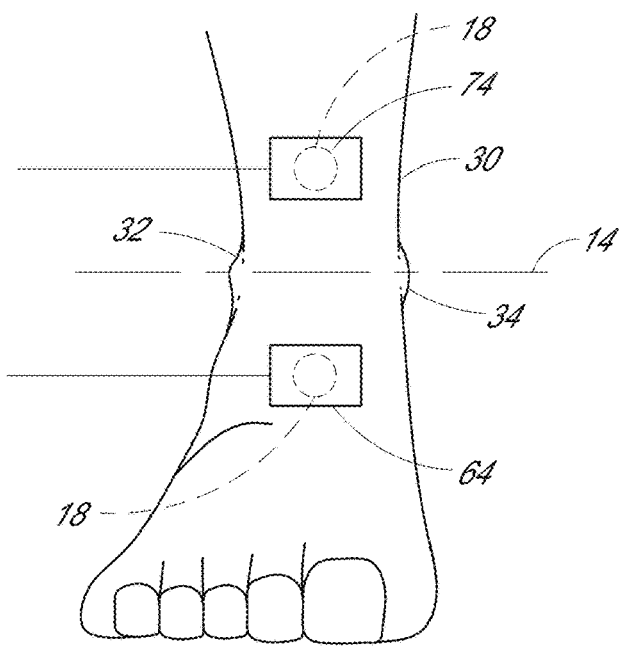
FIG. 3 is an enlarged view illustrating an ankle portion of a leg with electrode pads, which is shown in FIG. 1.

Measuring body compositions of disabled or unhealthy people may be different from that for healthy persons. A healthy person may measure the body composition by standing on a body composition measurement apparatus like the system disclosed in U.S. Pat. No. 5,720,296. On the other hand, for hospitalized patients, someone else may have to attach electrode pads to the patient's body. FIGS. 1-3 show examples of electric measurements for a hospitalized patient. In FIGS. 1-3, electrode pads are attached to the patient and connected to a power supply and a voltage measurement system.

Repeated Measurements

For some patients, it may be necessary to measure body compositions repeatedly. In some embodiments, the measurements may be at regular intervals such as every several hours, every day, every other day, every week, etc.

Techniques for Repeated Measurements

Typically, as illustrated in FIGS. 1 to 3, electrode pads are attached to the subject's body and then detached after measurement. In repeated measurements, the electrode pads need to be attached at the same location of the subject's body for accuracy. In some embodiments, markings are made on the skin of the body to make sure that the electrode pads are attached to the same locations. In other embodiments, the electrode pads may be placed over or with reference to a visibly unique portion of the body such a scar or bone.

Marking Examples Near Ulnar Head and Malleolus

In embodiments, a marking can be made with reference to an ulnar head of an arm. For example, a line, dot or any marking can be drawn to mark an exact location near the ulnar head. FIGS. 1 and 2 show an example in which the markings 16 are drawn with reference to an imaginary line 12 passing the ulnar head 22 generally perpendicular to the longitudinal direction of the arm. The markings 16 may be invisible after the electrodes 62 and 72 are attached as the electrode pads cover the markings as shown in FIGS. 1 and 2. Similarly, a marking is made with reference to a medial malleolus or a lateral malleolus of a leg. For example, as illustrated in FIGS. 1 and 3, markings 18 can be made near the lateral malleolus 32 or medial malleolus 34 with reference to the imaginary line 14 passing the malleolus 32 or 34 generally perpendicular to the longitudinal direction of the leg. The markings 18 may be invisible after the electrode pads 64 and 74 are attached as the electrode pads cover the markings as shown in FIGS. 1 and 3.

Inconvenience and Other Issues

Repeated attaching and detaching electrode pads can be inconvenient. Even with markings, the location of attachment may vary, depending upon the level of care. Markings can be erased or damaged. Wires can be tangled. The contact of the electrode pads may not be good when the surface is wet.

Clamp Electrode Apparatus

Figure 4:
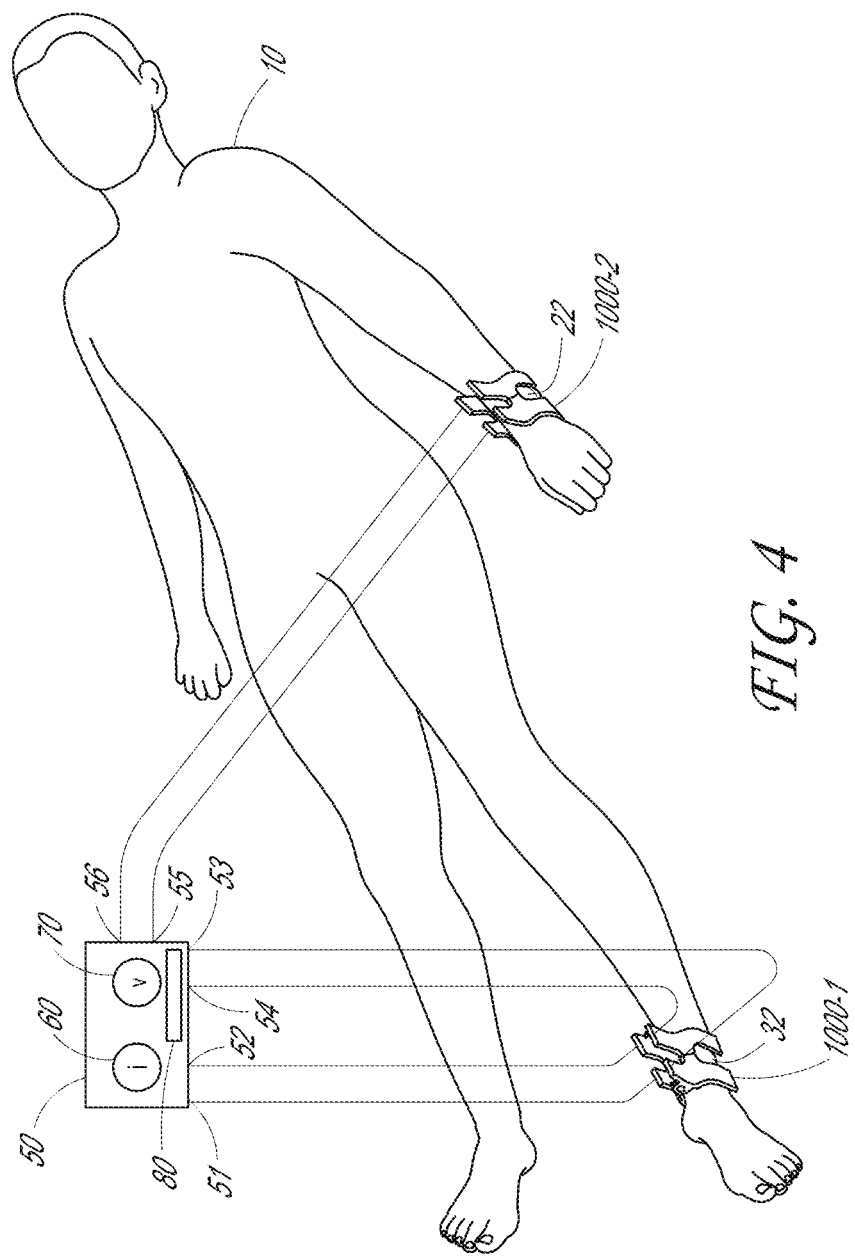
FIG. 4 is a schematic view illustrating a body composition measurement configuration according to embodiments of the invention.
Figure 5:
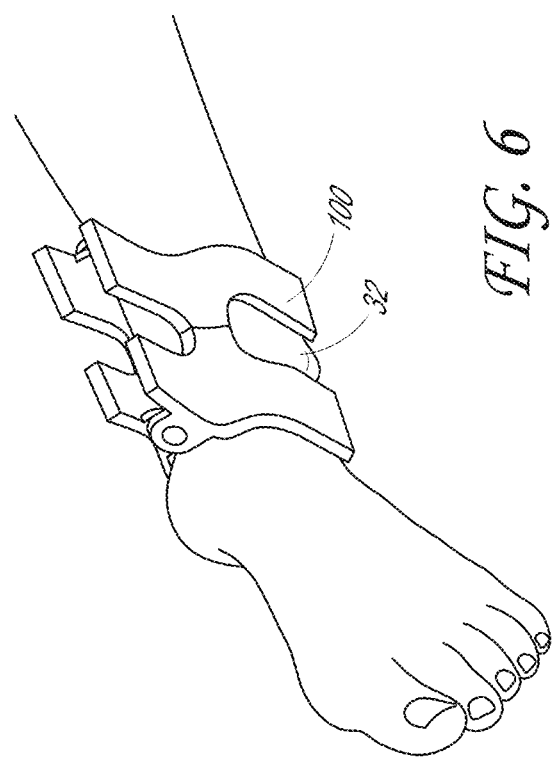
FIG. 5 is a perspective view illustrating a wrist of an arm clamped with a clamp electrode apparatus in the body composition measurement shown in FIG. 4.
Figure 6:
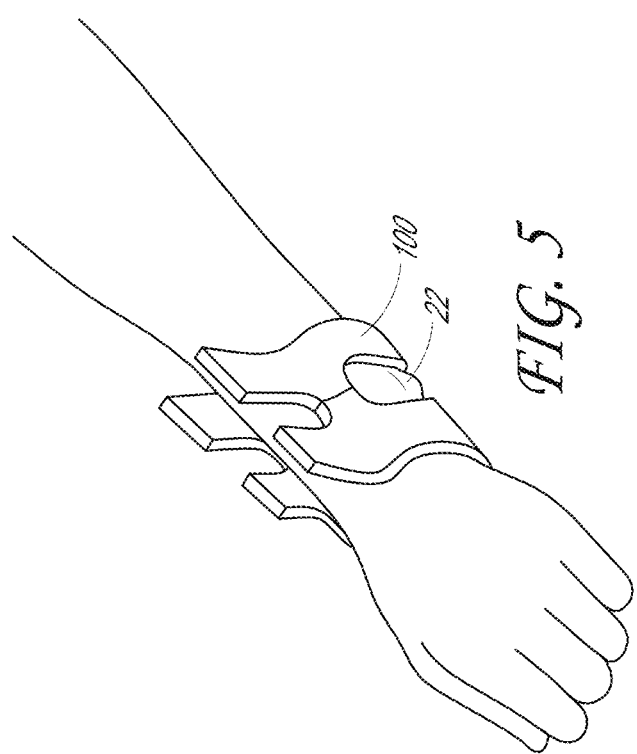
FIG. 6 is a perspective view illustrating an ankle of a leg with a clamp electrode apparatus in the body composition measurement shown in FIG. 4.

In embodiments, a clamp electrode apparatus is provided to address the issues of repeated measurements. Referring to FIGS. 4 to 6, the clamp electrode apparatus grips a wrist or an ankle of the subject for the body composition measurements. The clamp electrode apparatus can also be referred to as an electrode clamp, an electrode clip or a clip electrode apparatus.

Measurement while Subject Lies on the Back

In embodiments, referring to FIG. 4, body compositions are measured while a subject lies on the back, and the invention is not limited thereto. In another embodiment, the body compositions may be measured while the subject sits.

Two Clamps in a Clamp Electrode Apparatus

Figure 7:
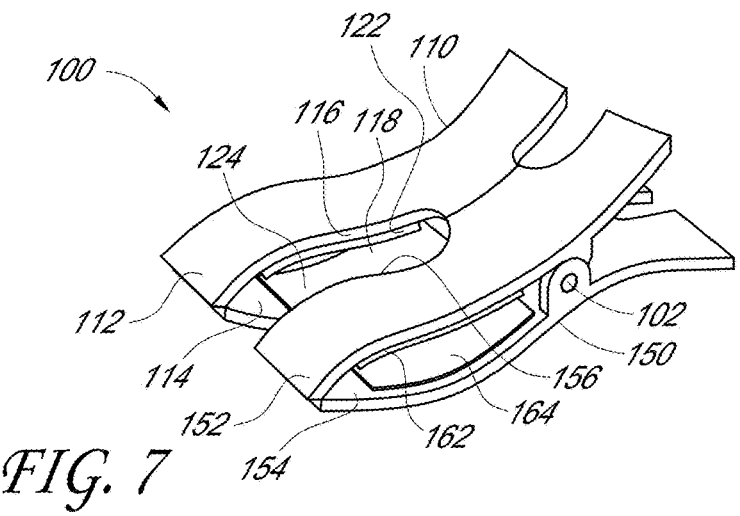
FIG. 7 is a perspective view of a clamp electrode apparatus according to embodiments of the invention.
Figure 8:
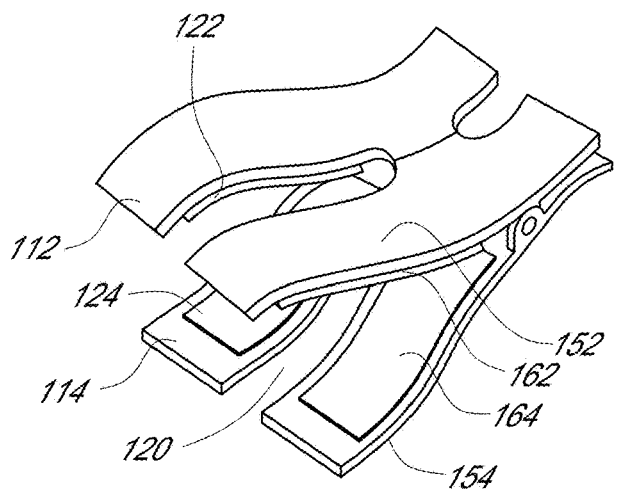
FIGS. 8 and 9 are perspective views of the clamp electrode apparatus shown in FIG. 7, showing different states of operation.
Figure 9:
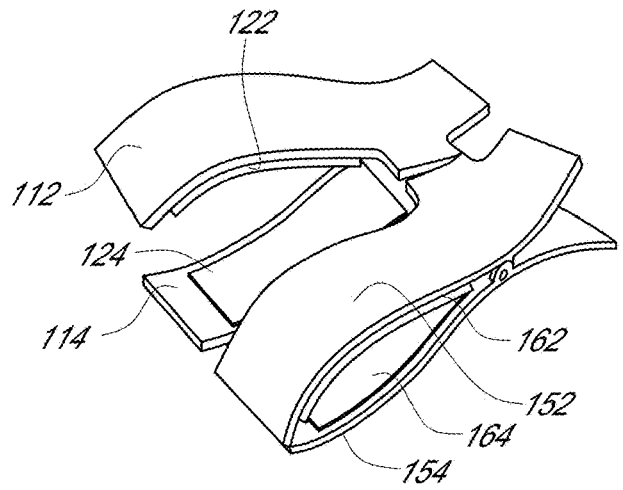

In embodiments, referring to FIGS. 7 to 9, the clamp electrode apparatus 100 includes a first clamp 110 and a second clamp 150 that are arranged side by side. The first clamp 110 and the second clamp 150 are connected to each other to form an integrated apparatus.

Clamp Bodies

In embodiments, referring to FIGS. 7 to 9, the first clamp 110 has an upper clamp body 112 and a lower clamp body 114. The second clamp 150 also has an upper clamp body 152 and a lower clamp body 154. The upper clamp body and the lower clamp body of each of the clamps 110 and 150 are hingedly connected with and movable relative to each other. Accordingly, the first clamp 110 and the second clamp 150 can grip a limb portion (for example, a wrist or ankle) of a subject by moving the upper clamp body and the lower clamp body relative to each other. The terms "upper" and "lower" do not refer to their absolute location. In some circumstances, for example, an item labeled with term "upper" may be located lower or under an item labeled with the term "lower."

Hinged Connection of First Clamp and Second Clamp

In embodiments, referring to FIGS. 7 to 9, the upper clamp body 112 and the lower clamp body 114 of the first clamp 110 are hingedly connected with each other. Accordingly, the upper clamp body 112 may rotate around a hinge axis with respect to the lower clamp body 114. In embodiments, a spring is provided to bias the upper clamp body 112 and the lower clamp body 114 to close such that the first clamp 110 can grip a limb portion with resilient force of the spring. Similarly, the upper clamp body 152 and the lower clamp body 154 of the second clamp 150 are also hingedly connected with each other, and thus, the upper clamp body 152 may rotate with respect to the lower clamp body 156. Another spring is provided to bias the upper clamp body 152 and the lower clamp body 154 to grip the limb portion with resilient force.

Hinge Axis of First Clamp and Second Clamp

In embodiments, referring to FIGS. 7 to 9, one hinge pin 102 extends to penetrate the first clamp 110 and the second clamp 150 so that the clamp bodies rotate around a single hinge axis. In other embodiments, the hinge axis of the first clamp and the hinge axis of the second clamp may be different from each other. In this case, the two hinge axes may be approximately parallel to each other. In some other embodiments, the two hinge axes are not parallel to each other.

Independent Movements of First Clamp and Second Clamp

In embodiments, as shown in FIG. 9, when clamping, the first clamp 110 and the second clamp 150 are operable independently from each other. Thus, the clamp electrode apparatus can grip a limb portion even if the thickness of the limb portion at the grip location of the first clamp is different from that at the grip location of the second clamp. In embodiments, both the first and second clamps can be operated at the same time as shown in FIG. 8.

Clamp Electrode Apparatus Used for an Ankle and a Wrist

In embodiments, the configuration of a clamp electrode apparatus used for an ankle may be identical or similar to that of a clamp electrode apparatus used for a wrist. In one embodiment, the size of the clamp electrode apparatus for an ankle is bigger than that of the clamp electrode apparatus for a wrist while the configurations are substantially the same. In some embodiments, the configuration of the clamp electrode apparatus for an ankle may be different from that of a clamp electrode apparatus for a wrist. For example, in the clamp electrode apparatus for an ankle, the hinge axes of the first and second clamps are not parallel to each other and/or form together an angle less than 180° to conform to the shape of the ankle.

Formation of Channel or Opening

In embodiments, as illustrated in FIG. 7, the clamp electrode apparatus includes a channel or opening 118. The first clamp 110 and the second clamp 150 of the clamp electrode apparatus 100 are arranged side by side such that an inner edge 116 of the upper clamp body 112 of the first clamp 110 and an inner edge 156 of the upper clamp body 152 of the second clamp 150 face each other. The inner edges 116 and 156 are spaced from each other to define the opening or channel 118 therebetween. In embodiments, the channel can be defined by two parallel edges 116 and 156 as shown in FIG. 7. In other embodiments, two semi-circular edges may define a circular opening.

Aligning Channel or Opening to a Reference Mark on a Limb

In embodiments, the opening or channel 118 is used to place the clamp electrode apparatus 100 at a target location on a limb in reference with a reference mark, e.g., an ulnar head or malleolus. Specifically, when gripping a limb portion with the clamp electrode apparatus 100, the clamp electrode apparatus 100 is arranged such that the reference mark is placed within the channel 118. For example, when clamping a wrist, the clamp electrode apparatus 100 is located and grips the wrist such that an ulnar head of the wrist is placed within the opening or channel 118. When clamping an ankle, the clamp electrode apparatus 100 is located and grips the ankle such that a malleolus of the ankle is placed within the opening or channel 118.

Adjustment of Gripping Location with Reference to Reference Mark

In embodiments, while clamping a limb with the clamp electrode apparatus, a user can check if the reference mark is being located in the channel. When the reference mark is misaligned with respect to the channel, the user can move the clamp electrode apparatus and adjust the position or orientation of the clamp electrode apparatus such that the reference mark is located within the channel. Repeated measurements require repetition of clamping and unclamping operations of the clamp electrode apparatus. Use of the channel and the reference mark allows the clamp electrode apparatus to grip the same location of the limb with or without ignorable or tolerable errors.

Clamping Wrist and Ankle Using Ulnar Head or Malleolus as Reference Mark

In embodiments, referring to FIG. 5, when a user clamps or grips a wrist with the clamp electrode apparatus 100, the user may use the ulnar head 22 as a reference mark. The user may open the first and second clamps of the apparatus 100 and place the wrist within the opened clamps. To grip the same location of the wrist, the user may adjust the location or the orientation of the clamp electrode apparatus 100 while checking if the ulnar head is shown through the channel. After confirmation of the alignment, the user releases the first and second clamps such that the ulnar head is placed within the channel and the apparatus 100 grips the wrist. Similarly, referring to FIG. 6, when the user clamps an ankle with the clamp electrode apparatus 100, the user may use the malleolus 32 as the reference mark. Both or either of the mesial malleolus and the lateral malleolus can be used. When gripping the ankle, the apparatus 100 is arranged and clamped on the ankle such that the malleolus 32 is placed within the channel.

Ulnar Head or Malleolus as a Guide

In embodiments, the reference marks such as an ulnar head and malleolus may be used as a guide. When the reference mark is slightly misaligned with the opening or channel, the position and orientation of the clamp electrode apparatus may be adjusted by guidance of the reference mark. For example, the generally conical malleolus may be used as a guide surface. When there is slight misalignment between the channel and the malleolus, the edge 116 or 156 (see FIG. 7) may contact and slide on the slanted surface of the malleolus. Thus, the clamp electrode apparatus can adjust its position and/or orientation until the top portion of the malleolus is located at the middle of the channel 118 between two edges 116 and 156.

Opening or Channel Between Lower Clamp Bodies

As shown in FIGS. 7 to 9, in embodiments, an opening or channel 118 may be defined between the upper clamp bodies 112 and 152, and another opening or channel 120 may be defined between the lower clamp bodies 114 and 154. A reference mark of a limb may have a protruding direction different from the protruding directions of the reference marks in other limbs. For example, the protruding direction of the ulnar head of the right arm is opposite to the protruding direction of the ulnar head of the left arm. The configuration of the clamp electrode apparatus having a channel between the upper clamp bodies and another channel between the lower clamp bodies allows the clamp electrode apparatus to grip a limb without being constrained by protruding direction of the reference marking of the limb.

Artificial Reference Mark

A specific body portion, such as, ulnar head or malleolus, already present on a subject body may be used as a reference mark. However, the invention is not limited thereto. For example, a portion in which a bone protrudes like the ulnar head or the malleolus can be used as a reference mark. The reference mark may originally be present in the subject body or may be a mark artificially prepared at a specific position of the body. Such an artificial mark may be a protruding structure or a visible mark such as a point, a circle, a polygon, a symbol X or the like expressed to be distinguishable with eyes although it does not protrude.

Restriction of Movement of Clamp Electrode Apparatus by Reference Mark

In embodiments, the reference mark has a protruding structure. Movement of the clamp body can be restricted by the protruding structure after gripping a limb having the reference mark with the clamp electrode apparatus. Specifically, a movement of the clamp electrode apparatus along the longitudinal direction of the limb can be restricted as the reference marking abuts the edges forming the channel and restricts the movement. Referring to FIG. 5, for example, when the ulnar head 22 is within the channel, a movement of the clamp body along the longitudinal direction of the arm may be restricted since the ulnar head contacts with inner edges 116 and 156 of the clamp body. Referring to FIG. 6, in embodiments, the malleolus 32 may restrict a movement of the clamp electrode apparatus.

Four Electrodes

In embodiments, referring to FIGS. 7 to 9, the clamp electrode apparatus 100 has a first electrode 122, a second electrode 152, a third electrode 124 and a fourth electrode 154. In the illustrated embodiments, electrode pads are attached to inside the first and second clamps to provide the first to fourth electrodes 122, 152, 124 and 154. Specifically, the first electrode 122 is attached to the upper clamp body 112 of the first clamp 110, and the third electrode 124 is attached to the lower clamp body 114 of the first clamp 110. The second electrode 162 is attached to the upper clamp body 152 of the second clamp 150, and the fourth electrode 164 is attached to the lower clamp body 154 of the second clamp 150. In some embodiments, the electrodes are embedded in the upper lower bodies of the first and second clamps.

Locations of Electrodes

In embodiments, referring to FIGS. 7 to 9, the first electrode 122 and third electrode 124 face each other while the second electrode 162 and the fourth electrode 164 face each other. Specifically, the first electrode 122 and the third electrode 124 are attached to the upper clamp body 112 and the lower clamp body 114, respectively. The distance between the first electrode 122 and a reference point (e.g., a point at the edge 116) as measured along the hinge axis is substantially the same with that between the third electrode 124 and the same reference point. Accordingly, when the clamp electrode apparatus 100 grips a target portion of a limb (e.g., a wrist or ankle), the first electrode 122 and the third electrode 124 contact skin at locations which are generally equidistantly spaced from the reference mark as measured along the longitudinal direction of the limb. Similarly, referring to FIGS. 7 to 9, the second electrode 162 and the fourth electrode 164 are attached to the upper clamp body 152 and the lower clamp body 154, respectively, such that the distance between the second electrode 162 and a reference point (e.g., a point at the edge 156) as measured along the hinge axis is substantially the same with that between the fourth electrode 164 and the same reference point. Accordingly, when the clamp electrode apparatus 100 grips the target portion of the limb, the second electrode 162 and the fourth electrode 164 contact skin at locations which are generally equidistantly spaced from the reference mark as measured along the longitudinal direction of the limb.

Connection of Electrodes to Measurement System

In embodiments, referring to FIG. 4, each of the electrodes may be connected to a terminal of the measurement system 50 using wires or cables. When measuring, all four electrodes may be connected to the terminals of the measurement system 50. In embodiments, only some of the electrodes may be connected. For example, only a pair of electrodes, e.g., the first electrode 122 and the third electrode 124 or the first electrode 122 and the second electrode 162, may be connected to the terminals of the measurement system 50.

Electrodes Contacting the Same Skin Portions in Repetitive Measurements

In embodiments, referring to FIGS. 5 to 9, the first electrode 122, the second electrode 162, the third electrode 124 and the fourth electrode 164 of the clamp electrode apparatus 100 contact different locations. As discussed above, the clamp electrode apparatus 100 has an opening or channel and grips a limb such that a reference mark (e.g., an ulnar head or malleolus) of the subject body is placed within the channel. Accordingly, even in repetitive measurements which require repetitive clamping and unclamping of the clamp electrode apparatus 100, the clamp electrode apparatus 100 can grip the substantially same portion of the limb by cooperation of the channel and the reference mark. Thus, each of the first electrode, the second electrode, the third electrode and the fourth electrode contact the generally same location of the limb in the repetitive measurements.

Repeatability of Measurement

As discussed above, the electrodes contact nearly the same locations in the repeated measurements. Thus, substantially the same results of the body composition measurement can be obtained when assuming that there is no change in the body compositions and a measurement environment. Since the measurements have repeatability as above, changes in the body compositions can be identified when comparing the result of a body composition measurement on a certain day with the results of the other days. Thus, based on results of measurements repeated at regular intervals (e.g., every day, every other day, once a week or once a month), a doctor may determine that the body composition is changed. Based on the determination, a doctor may further change a treatment method and/or medicine for the subject or may change an exercise program of the subject.

Measurement System

For measuring body composition, a measurement system is connected to the clamp electrode apparatus. In embodiments, referring to FIG. 4, the measurement system 50 has one or more current source circuits or devices 60 and one or more voltage measurement circuits or devices 70. The measurement system 50 also has terminals for connection of electrodes of the clamp electrode apparatus. Moreover, the measurement system 50 is provided with one or more switching circuits or devices 80 for switching connection between the terminals and the current source 60 or the terminals and the voltage measurement apparatus 70. In embodiments, referring to FIG. 4, the measurement system 50 may further have one or more processors and one or more memories, one or more storages, a display, a printer, etc. The memory stores one or more programs for controlling various devices or circuits included in the measurement system 50. Such programs can further process data and analyze body compositions.

Terminals

In embodiments, referring to FIG. 4, the measurement system 50 has a first terminal 51, a second terminal 52, a third terminal 53, a fourth terminal 54, a fifth terminal 55 and a sixth terminal 56. The number of terminals is not limited thereto. For example, the measurement system 50 may further have one or more additional terminals. In another example, the measurement system 50 may have electrodes less than six as in the measurement system shown in FIG. 20. The number of terminals may be equal to that of electrodes in clamp electrode apparatuses to be used. In a further example, the number of terminals may be greater or smaller than the number of electrodes.

Switching Circuit

The measurement system 50 further has the one or more switching circuits 80. The switching circuit connects the terminals to the current source circuit or the voltage measurement circuit and performs a switching function by connecting and disconnecting the terminals to/from the circuits 60 and 70 during measurements. As shown in FIG. 4, when a clamp electrode apparatus 1000-1 grips an ankle of a leg and another clamp electrode apparatus 1000-2 grips a wrist of an arm, the switching circuit 80 is configured to perform a switching function of connecting the terminals to the current source circuit 60 or the voltage measurement circuit 70 or disconnecting the terminals from the circuits 60 and 70.

Electrical Measurements

Figure 10:
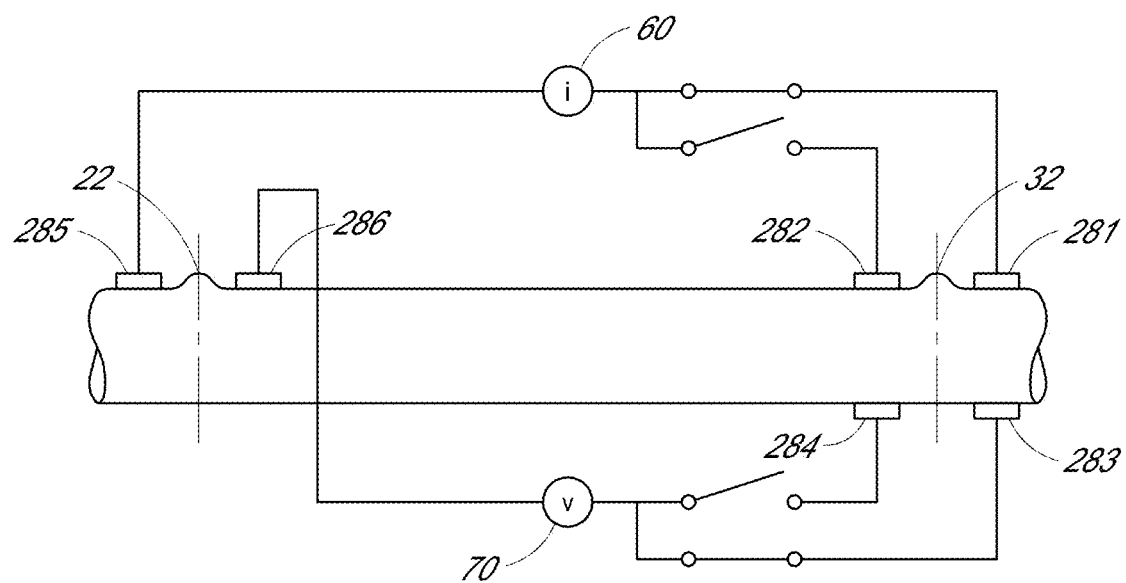
Figure 11:
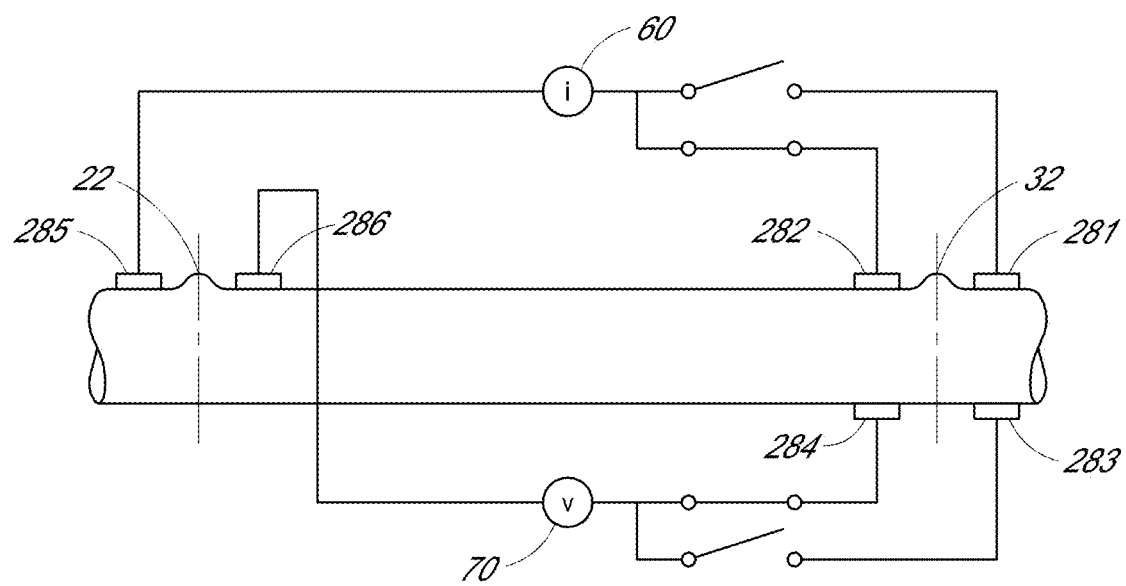

Referring to FIGS. 4, 10 and 11, in order to analyze body compositions of a subject body, electrical measurements are first performed on the subject using the electrical measurement system 50. After clamping the clamp electrode apparatuses on the limbs of the subject body and connecting the electrodes of the clamp electrode apparatus to the terminals of the measurement system, the electrical measurement is performed by connecting the terminals to a current source 60 and a voltage measuring circuit 70 using the switching circuit 80. In some embodiments, the electrical measurements are performed while changing the connection of the terminals with the current source 60 and the voltage source 70 by operating the switching circuit 80.

Clamping with Clamp Electrode Apparatus for Electrical Measurements

In embodiments, referring to FIG. 4, a clamp electrode apparatus 1000-1 grips an ankle of a subject so that the malleolus 32 is positioned within an opening or channel of the apparatus 1000-1. When gripping, a user clamps the ankle with the clamp electrode apparatus while visually checking or confirming whether the mark is placed within the channel 118. When the clamp electrode apparatus 1000-1 is clamped, the four electrodes 281, 282, 283 and 284 contact the locations around the ankle. Similarly, a clamp electrode apparatus 1000-2 grips a wrist of the subject body. The electrodes of the clamp electrode apparatus 1000-2 also contact the locations of the wrist.

Connection Between Terminals and Electrodes for Electrical Measurements

In embodiments, referring to FIGS. 4, 10 and 11, the electrodes are connected to the terminals before or after clamping the wrist and ankle with the clamp electrode apparatuses. Specifically, the electrode 281 is connected to the first terminal 51, the electrode 282 is connected to the second terminal 52, the electrode 283 is connected to the third terminal 53, the electrode 284 is connected to the fourth terminal 54, the electrode 285 is connected to the fifth terminal 55, and the electrode 286 is connected to the sixth terminal 56.

Measuring in Two Different Measurement Settings

In embodiments, referring to FIGS. 4, 10 and 11, electrical measurements are performed on a body portion including an arm, trunk and leg. In the illustrated embodiments, a clamp electrode apparatus having electrodes 285 and 286 grips a wrist and the electrodes 285 and 286 contact locations around the wrist. Another clamp electrode apparatus having electrodes 281, 282, 283 and 284 grips an ankle and the electrodes 281, 282, 283 and 284 contact the locations around the ankle. The measurement is performed in the first measurement setting as shown in FIG. 10 and the second measurement setting in FIG. 11. For transitioning between the two measurement settings, electrical connections between the terminals and the circuits 60 and 70 are switched with the switching circuit 80 to provide the two different measurement settings. Thus, the transitioning does not require unclamping and re-clamping the clamp electrode apparatus.

Measuring in the First Measurement Setting

FIG. 10 illustrates a first measurement setting for performing an electrical measurement on the body. The first measurement setting is formed by connecting the electrode 281 and the electrode 285 to the current source circuit 60 and connecting the electrode 283 and the electrode 286 to the voltage measurement circuit 70 by operation of the switching circuit 80. As illustrated, in the first measurement setting, a body portion forming an electric connection between the electrodes 283 and 285 includes the ankle. In the state shown in FIG. 10, the voltage measurement circuit 70 measures a first voltage drop or difference between the electrode 283 and the electrode 286 while the current source circuit 60 supplies a current between the electrode 281 and the electrode 285. The first voltage difference is a value measured for the body portion including the ankle.

Measuring in the Second Measurement Setting

Then, the switching device 80 switches the connection of the circuit such that the measurement system 50 performs an electrical measurement on the body portion which does not include the ankle. FIG. 11 illustrates a second measurement setting. Specifically, in the second measurement setting, the switching circuit 80 provided in the measurement system 50 disconnects the connection of the electrode 281 and the electrode 283. Further, the switching circuit 80 connects the electrode 282 to the current source circuit 60 and the electrode 284 to the voltage measurement circuit 70. The connection of the electrode 285 and the electrode 286 is maintained as it is in the first measurement setting. In the state shown in FIG. 11, a second voltage drop or difference is measured between the electrode 284 and the electrode 286 connected to the voltage measurement circuit 70 while supplying a current between the electrode 282 and the electrode 285 connected to the current source circuit 60. The second voltage difference measured in the second measurement setting is a value measured for the body portion excluding the ankle.

Another Embodiment of Second Measurement Setting

In another embodiment, the second measurement setting may be formed by disconnecting the connection between the electrode 283 and the voltage measurement circuit 70 and connecting the electrode 284 to the voltage measurement circuit 70 while maintaining the connection between the electrode 281 and the current source circuit 60. In this state, the second voltage difference is measured between the electrode 284 and the electrode 286 connected to the voltage measurement circuit 70 while supplying a current between the electrode 281 and the electrode 285.

Switching Between the First and Second Measurement Settings while Maintaining Clamping State In embodiments, referring to FIGS. 4, 10 and 11, switching from the first measurement setting to the second measurement setting is achieved while maintaining the clamp electrode apparatuses gripping the ankle and the wrist. It can be performed without unclamping the clamp electrode apparatus between the first measurement and the second measurement.

Calculation of Impedance and Body Composition Analysis

In embodiments, impedances of body portions can be calculated using the voltage drops obtained in the first and second measurement settings. Body compositions of the subject may be analyzed using a formula or look-up table by applying the obtained impedances to the formula or the table. The formula may be, for example, various formulas disclosed in U.S. Pat. No. 5,720,296 (Inventor: Ki Chul Cha). A method of using impedance in a body composition analysis as disclosed in the above patent is incorporated herein by reference.

Calculation of Impedance of Ankle

An impedance of an ankle can be obtained using the voltage drops acquired in the first and second measurement settings. In embodiments, first impedance may be obtained by processing a first voltage difference measured in the first measurement setting shown in FIG. 10. Second impedance may be obtained by processing a second voltage difference measured in the second measurement setting shown in FIG. 11. Since the first measurement setting includes the ankle and the second measurement setting does not include the ankle, for example, an impedance of the ankle of the subject may be obtained from a difference between the first impedance and the second impedance. In another embodiment, the impedance of the ankle may be obtained by inputting the first voltage difference and the second voltage difference into a prepared formula. The impedance of an ankle can be used for body composition analysis.

Supply of Currents Having Different Frequencies

In embodiments, referring to FIGS. 4, 10 and 11, in the measurement system 50, the voltage measurement apparatus 70 may measure a voltage difference between electrodes while the current source 60 supplies an AC current between the electrodes. When the measurements are made in the first and second measurement settings, the current source 60 may sequentially supply currents having different frequencies. The voltage measurement apparatus 70 may measure voltage drops corresponding to the different frequencies between the electrodes while the currents of different frequencies are sequentially supplied. In embodiments, each voltage difference may be expressed as an electrical signal. The frequencies of the sequentially supplied currents may be, for example, 1 kHz, 5 kHz, 50 kHz, 250 kHz and 500 kHz.

Impedances for Respective Frequencies and Use Thereof

In embodiments, impedances for respective frequencies are obtained by processing current signals of different frequencies applied between the current electrodes by the current source 60 and by processing voltage signals of respective frequencies obtained by the voltage measurement apparatus 70. The body compositions of the subject may be analyzed by processing the impedances for the respective frequencies using a pre-prepared formula or look-up table. Generally, a high frequency electrical current signal has a characteristic of better penetration through cell walls than a low frequency electrical current signal. Impedance measured while applying a high frequency current may be a value on which the amount of water in a cell is reflected. Accordingly, a result of a body composition analysis using all the impedances of all frequencies may more accurately show an actual body composition condition of the subject.

Edema

Generally, when a patient suffers from edema, it is noticeable at the patient's ankle. A doctor diagnoses edema by pressing skin around the ankle with a finger. In embodiments, referring to FIGS. 4, 10 and 11, the edema may be diagnosed using the measurement apparatus and the clamp electrode apparatuses, since the analysis of the body compositions (e.g., the amount of water) of the ankle enables determination of the possibility of edema.

Determination of Probability of Edema Using Magnitude of Impedance of Ankle

Generally, the impedance of the ankle as obtained in the embodiments discussed above has a correlation with the amount of water in the ankle. Accordingly, the impedance of the ankle may be an index for determining edema. In embodiments, edema may be determined based on the magnitude of the impedance. For example, if the impedance of the ankle is smaller than a predetermined value, it is determined that there is a possibility of edema.

Determination of Edema Using Trend of Impedance of Ankle

In another embodiment, edema may be determined based on the trend of the impedance. When the clamp electrode apparatus used in the embodiments described above is used, the electrodes may be placed on and contact the same skin portions used in repetitive measurements, and thus a trend of the impedances may be obtained with a considerable degree of accuracy. In embodiments, if the impedance of the ankle is maintained at a constant level and then decreases greatly, this may be determined as a possibility of edema.

Determination of Edema Using Electrical Signal with Different Frequencies

Generally, edema may be caused by an increase of water outside a cell rather than an amount change of water within the cell. In addition, a high frequency electrical signal has a characteristic of better penetration through a cell wall than a low frequency electrical signal. Accordingly, in embodiments, edema may be determined using a low frequency electrical signal (e.g., an electrical signal of 5 kHz) and a high frequency electrical signal (e.g., an electrical signal of 500 kHz), which have relatively different frequencies. While the low frequency electrical signal is applied, a first voltage difference may be obtained, and while the high frequency electrical signal is applied, a second voltage difference is obtained. Using the first and second voltage differences, impedances of the ankle for the low and high frequency electrical signals are obtained. In one embodiment, if a difference between an impedance measured using the low frequency electrical signal and an impedance measured using a high frequency electrical signal is greater than a predetermined value, it is determined as edema. In another embodiment, the edema may be determined by evaluating a change in the impedance of the ankle measured using the high frequency electrical signal and a change in the impedance of the ankle measured using the low frequency electrical signal. This determination can be provided by credible measurement results using the clamp electrode apparatus in repetitive measurements. In other embodiments, if a change rate of the impedance of the ankle measured using the high frequency electrical signal is greater than a change rate of the impedance of the ankle measured using the low frequency electrical signal by more than a preset value, this may be determined as edema.

Final Diagnosis and Treatment of Edema

When it is determined that there is a possibility of edema using an impedance of the ankle in the embodiments discussed above, a doctor finally determines edema using another diagnostic machine or diagnostic method (e.g., a diagnostic method using MRI scanning). If edema is finally determined, the doctor may treat the edema by prescribing a medicine for mitigating the edema. In embodiments, while an edema patient is treated, measurements can be periodically repeated to check development of edema.

Computer Program

In embodiments, referring to FIG. 4, a computer program is stored in a memory device of the measurement system 50. The computer program contains instructions for performing the measurement and the analysis as discussed above. In embodiments, the computer program contains instructions for causing a processor to operate the current source circuit 60, the voltage measurement circuit 70 and the switching circuit 80 for measuring voltage differences when a start button provided in the measurement system is pressed. Further, the instructions of the computer program cause the processor to process the measured voltage difference for obtaining an impedance and analyzing body compositions and to output the analysis results through an output device such as a display or printer.

Figure 12:
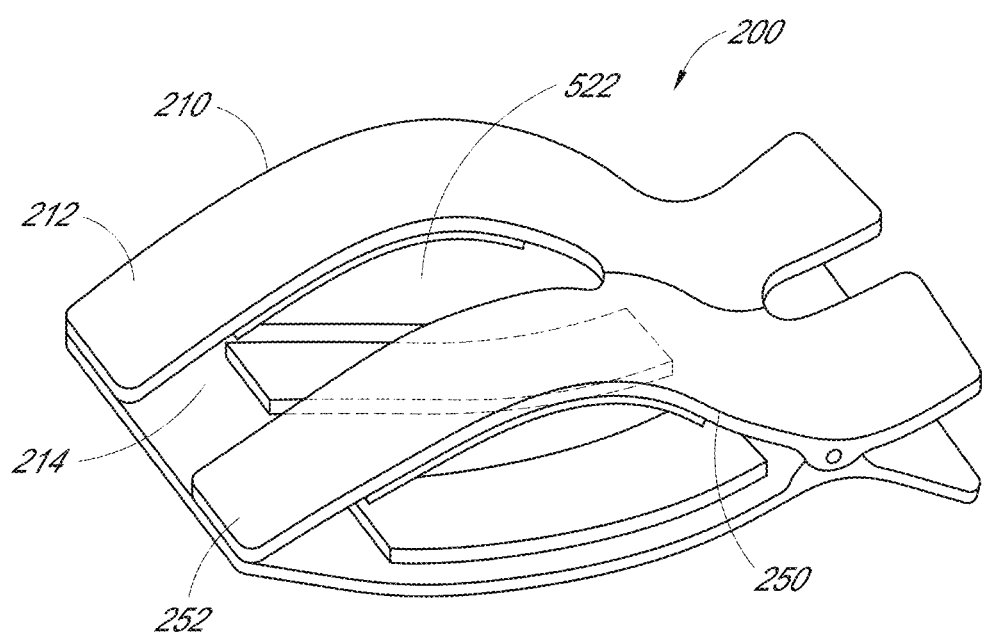
FIGS. 12 to 16 are perspective views of various clamp electrode apparatuses according to embodiments of the invention.

Another Embodiment—Clamp Electrode Apparatus of FIG. 12

In embodiments, referring to FIG. 12, an upper clamp body 212 of a first clamp 210 and an upper clamp body 252 of a second clamp 250 of a clamp electrode apparatus 200 are independently movable. On the contrary, the first clamp 210 and the second clamp 250 have an integrated lower clamp body 254. A channel 222 is defined between the upper clamp bodies. In another embodiment, a channel or opening performing the same function as the channel 222 shown in FIG. 12 may be defined at the center of the lower clamp body 254. In embodiments, referring to FIG. 12, one electrode is attached to each of the upper clamp bodies. Two electrodes are attached to the integrated lower clamp body to face the electrodes attached to the upper clamp bodies.

Figure 13:
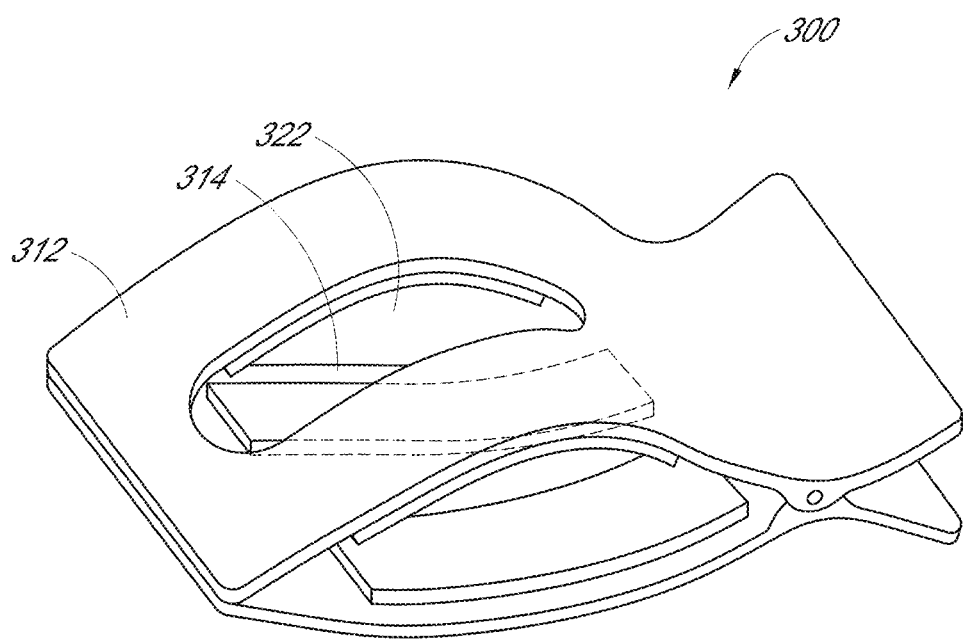

Further Embodiment—Clamp Electrode Apparatus of FIG. 13

In embodiments, referring to FIG. 13, a clamp electrode apparatus 300 has a single clamp. An opening 322 is formed at the center of the integrated upper clamp body 312 of the clamp. In another embodiment, a channel may be formed such that the upper clamp body has an open end. In a further embodiment, a channel or opening may be formed in the lower clamp body 314. In embodiments, referring to FIG. 13, electrodes are attached to the upper clamp body with the channel placed between the electrodes. Electrodes are attached to the lower clamp body at positions facing the electrodes attached to the upper clamp body.

Figure 14:
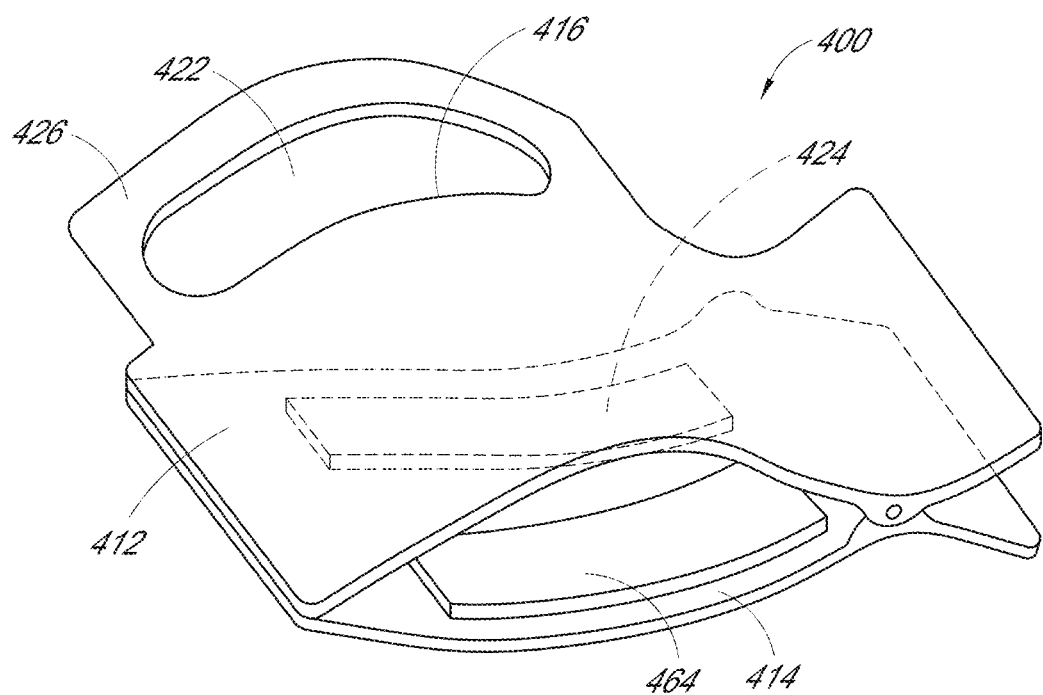
Figure 15:
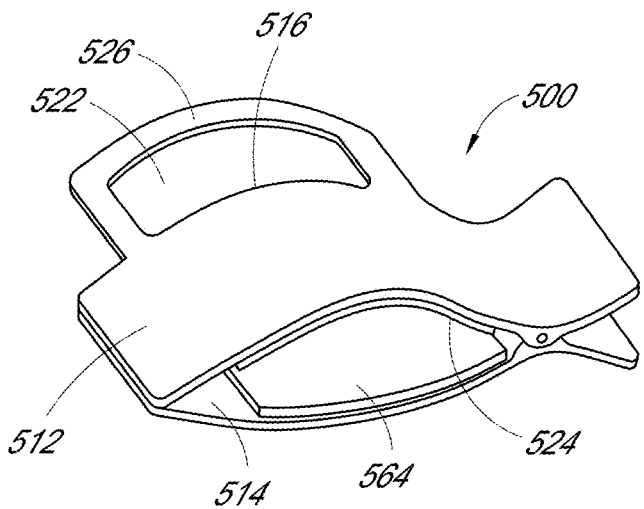

Still Further Embodiment—Clamp Electrode Apparatuses of FIGS. 14 and 15

In embodiments, referring to FIGS. 14 and 15, a clamp electrode apparatus 400 or 500 has a single clamp provided with an upper clamp body 412 or 512 and a lower clamp body 414 or 514. An opening 422 or 522 is formed at one side of the upper clamp body 412 or 512 while an opening 322 is formed in the middle of the upper clamp body 312 in FIG. 13. Specifically, an extension part 426 or 526 extending from an edge 416 or 516 of the upper clamp body is provided. A channel or opening 422 or 522 is formed between the extension part and the edge. The clamp electrode apparatus 400 or 500 is clamped at a specific position by aligning the opening 422 or 522 with a mark. The difference between the embodiment shown in FIG. 14 and the embodiment shown in FIG. 15 is positions of electrodes. In embodiments, referring to FIG. 14, both of the two electrodes 424 and 464 are placed on the lower clamp body 414. Alternatively, in embodiments, referring to FIG. 15, one electrode 524 is attached to the upper clamp body 512, and the other electrode 564 is attached to the lower clamp body 514. In another embodiment, the two electrodes may be attached to the upper clamp body side by side, and electrodes may be attached to the lower clamp body side by side to face the electrodes attached to the upper clamp body.

Use of Clamp Electrode Apparatuses Shown in FIGS. 14 and 15

In embodiments, when the clamp electrode apparatuses shown in FIGS. 14 and 15 are used, all the electrodes may contact locations on the skin positioned on either side of a reference mark when viewed in a direction perpendicular to a longitudinal direction of a limb. For example, when the clamp electrode apparatus is used on an arm, all the electrodes may contact locations of the skin positioned between the elbow and the ulnar head. When the clamp electrode apparatus is used on a leg, all the electrodes may contact locations of the skin positioned between the knee and the malleolus. Generally, when electrode contact locations are closer to the body trunk, the more accurate measurement can be made. Accordingly, when the apparatuses shown in FIGS. 14 and 15 described above are used, a more accurate measurement can be made. However, the invention is not limited thereto. In embodiments, all the voltage and current electrodes may be positioned on the side of a distal end of an arm or leg with respect to the position of the ulnar head or the malleolus.

Figure 16:
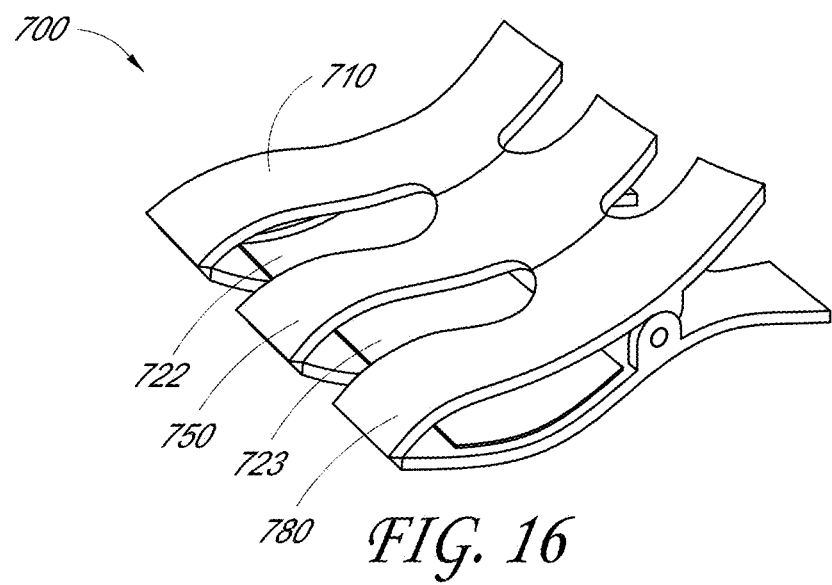

Further Embodiment—Clamp Electrode Apparatus of FIG. 16

A clamp electrode apparatus 700 shown in FIG. 16 is a configuration further having a third clamp 780 beside a second clamp 750 of the clamp electrode apparatus 100 shown in FIGS. 6 to 8. A channel 722 is formed between a first clamp 710 and the second clamp 750, a channel 723 is additionally formed between the second clamp 750 and the third clamp 780. The clamp electrode apparatus of this configuration may give a user more freedom in selecting a channel to be used.

Figure 17:
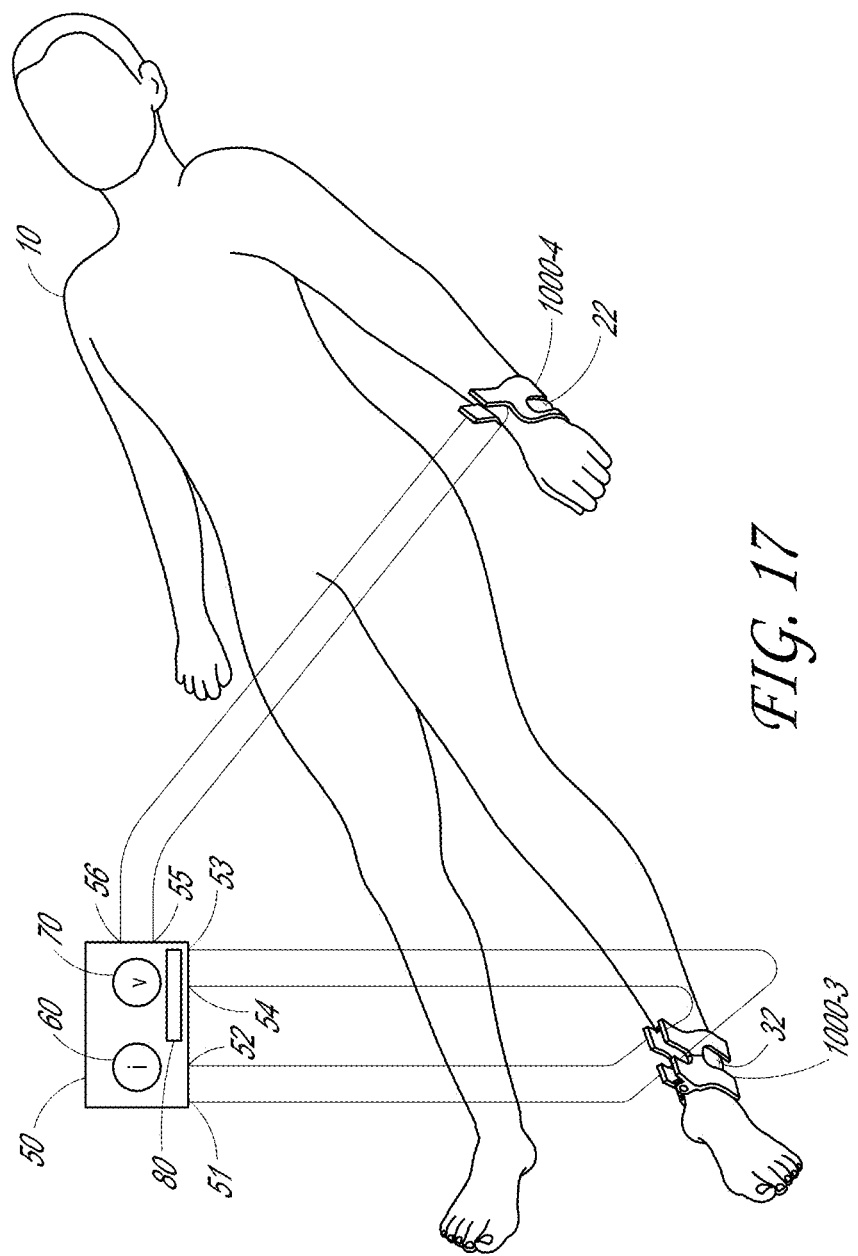
FIG. 17 is a schematic view of another body composition measurement configuration according to embodiments of the invention.
Figure 18:
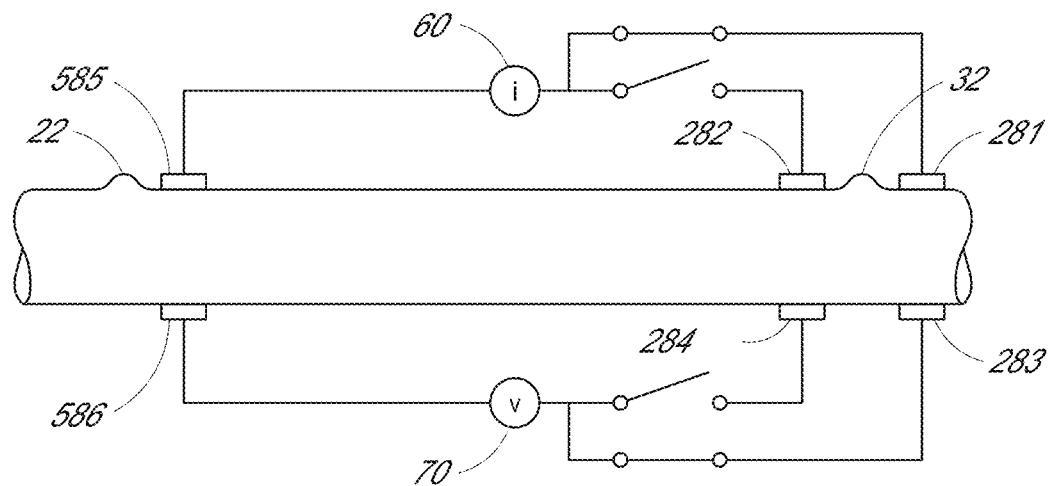
Figure 19:
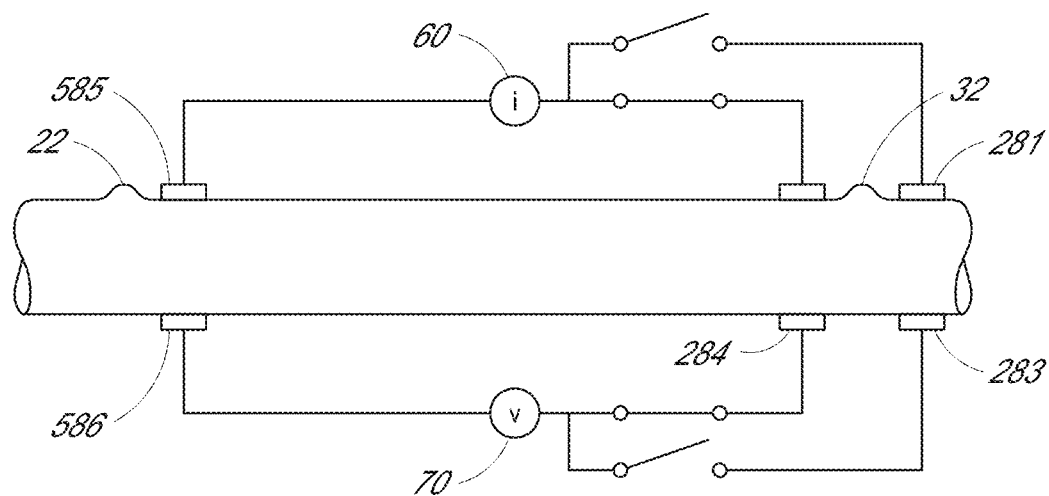

Electrical Measurement According to Embodiment Shown in FIGS. 17 to 19

The embodiment shown in FIGS. 17 to 19 provides a measurement setting almost identical to that of the embodiment shown in FIGS. 4, 10 and 11 except for the clamp electrode apparatus which is used for clamping a wrist. The clamp electrode apparatus 1000-4 clamped on the wrist as shown in FIGS. 17 to 19 has two electrodes 585 and 586. A clamp electrode apparatus 1000-3 clamped on an ankle may be the clamp electrode apparatuses shown in FIGS. 7 to 9, 12 and 13 as used in the embodiment shown in FIGS. 4, 10 and 11. The measurement setting shown in FIG. 18 corresponds to the first measurement setting shown in FIG. 10, and the measurement setting shown in FIG. 19 corresponds to the second measurement setting shown in FIG. 11. An electrical measurement using the measurement system 50 is substantially the same with that of the embodiment shown in FIGS. 4, 10 and 11.

Figure 20:
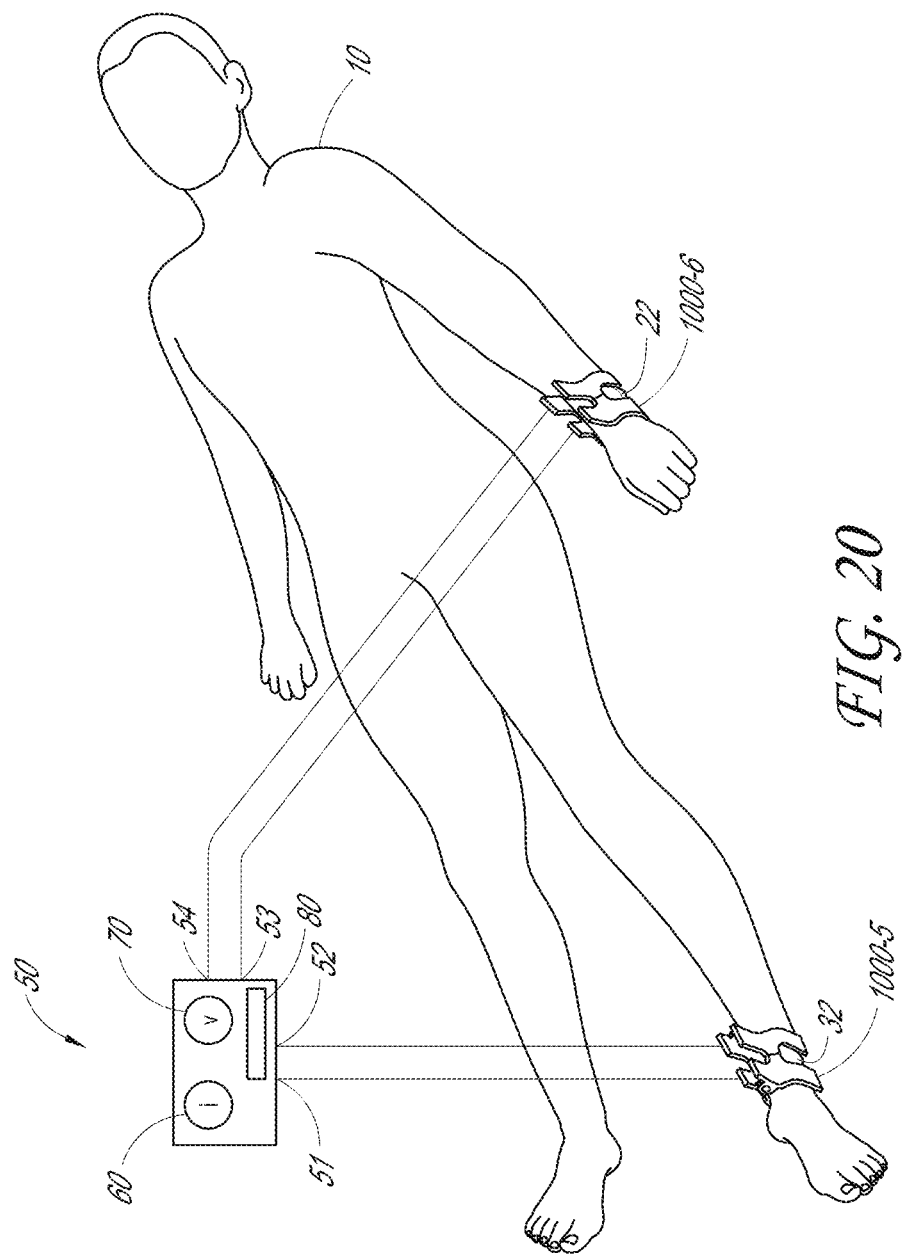
FIG. 20 is a perspective view illustrating a further body composition measurement configuration according to embodiments of the invention.

Electrical Measurement According to Embodiments Shown in FIG. 20

In an embodiment shown in FIG. 20, the measurement system 50 may have the same configuration as the embodiment shown in FIG. 4, except use of the first terminal 51, the second terminal 52, the third terminal 53 and the fourth terminal 54. As shown in FIG. 20, a clamp electrode apparatus 1000-5 is clamped on a leg, and another clamp electrode apparatus 1000-6 is clamped on an arm. The clamp electrode apparatuses 1000-5 and 1000-6 may be the clamp electrode apparatuses shown in FIGS. 7 to 9, 12 to 14 and 16.

Figure 21:
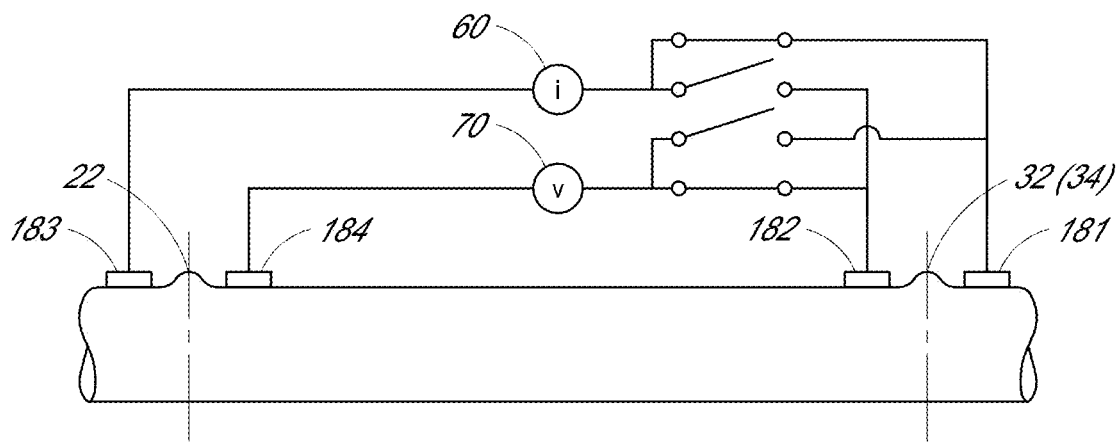

Formation of First Measurement Setting and Electrical Measurement Shown in FIG. 21

As shown in FIG. 21, the switching circuit 80 forms a first measurement setting by connecting the electrode 181 and the electrode 183 to the current source circuit 60 and by connecting the electrode 182 and the electrode 184 to the voltage measurement circuit 70. In this state, the voltage measurement circuit measures a first voltage difference between the electrode 182 and the electrode 184 while the current source 60 supplies a current between the electrode 181 and the electrode 183.

Figure 22:
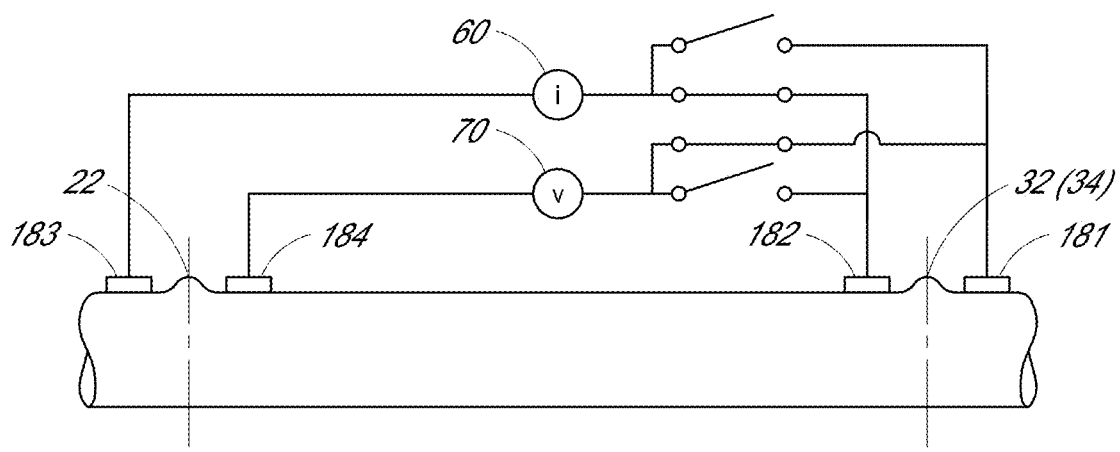

Formation of Second Measurement Setting and Electrical Measurement Shown in FIG. 22

After the measurement in the first measurement setting is completed, the switching circuit 80 switches the connection to a second measurement setting while maintaining the clamped states of the clamp electrode apparatuses 100-5 and 1000-6. As shown in FIG. 22, in the second measurement setting, the electrode 181 is connected to the voltage measurement circuit 70, and the electrode 182 is connected to the current source circuit 60. In this state, the voltage measurement apparatus 70 measures a second voltage difference between the electrode 181 and the electrode 184 while the current source 60 supplies a current between the electrode 182 and the electrode 183. Body compositions are analyzed by processing the first voltage difference and the second voltage difference as shown in the embodiments described above.

Embodiments of Electrical Measurement on Wrist or Another Portion of Limb

Although it has been described in the embodiments shown in FIGS. 4, 10, 11, 17 to 19 and 20 to 22 that impedances or body compositions of the ankle (specifically, an ankle portion between the electrodes attached respectively to two clamps of the clamp electrode apparatus) are measured using the first voltage difference and the second voltage difference, the invention is not limited to the electrical measurement of the ankle. In embodiments, an impedance or body composition of the wrist may be measured. Moreover, a trend of changes in the body compositions may be traced through repetitive measurements of the wrist. When the clamp electrode apparatus is clamped to measure the impedance or body composition of the wrist, the ulnar head may be used as a reference mark. Furthermore, impedances or body compositions of other portions of the arm or leg other than the wrist or the ankle and changes of the impedances or body compositions may be measured. For example, when a clamp electrode apparatus is clamped on a portion of the arm between an elbow and the wrist, a reference mark (e.g., an artificial mark made by coloring, taping or the like) is prepared at the forearm portion, and the clamp electrode apparatus may be mounted with reference to the reference mark.

Measurement of Impedance of Wrist

In embodiments, an impedance of a wrist may be obtained using a clamp electrode apparatus. Specifically, the clamp electrode apparatus is clamped such that the electrodes 281, 282, 283 and 284 shown in FIGS. 10 and 11 are in contact with the wrist region and another clamp electrode apparatus is clamped such that the electrodes 285 and 286 are in contact with the ankle. An impedance of the wrist may be obtained in the same method as the measurement of impedance at the ankle. Edema of the wrist may be diagnosed by processing the impedance of the wrist.

Although embodiments of the invention have been described above, those skilled in the art may understand that configurations of the various embodiments described above may be changed without departing from the spirit of the invention. It will be also understood that the changes fall within the scope of the invention.

What is claimed is:

1. A method of acquiring electrical measurements, the method comprising:

providing a measurement system comprising: a first clamp electrode apparatus mountable on a first limb of a subject, the first clamp electrode apparatus comprising:

a first clamp comprising a first upper clamp body and a first lower clamp body operably connected to each other such that the first upper and lower clamp bodies are movable relative to each other for clamping a first portion of the first limb of the subject between the first upper and lower clamp bodies;

a second clamp comprising a second upper clamp body and a second lower clamp body operably connected to each other such that the second upper and lower clamp bodies are movable relative to each other for clamping a second portion of the first limb adjacent the first portion between the second upper and lower clamp bodies;

the first and second clamps mechanically connected to form a single integrated device and arranged side by side such that a first edge of the first upper clamp body faces a second edge of the second upper clamp body and an opening or channel is defined between the first edge and the second edge, wherein the first upper clamp and the second upper clamp are apart from each other, wherein the opening or channel is configured to be positioned on the subject such that both the first edge and the second edge contact an ulnar head or malleolus to restrict a movement of the first clamp electrode apparatus along a longitudinal direction of the first limb when the first limb of the subject is clamped with the first clamp electrode apparatus;

a first electrode disposed on an inner surface of the first upper clamp body and configured to contact a first area of the first limb when the first limb is clamped with both the first and second clamps;

a second electrode electrically independent of the first electrode and disposed on an inner surface of the second upper clamp body and configured to contact a second area of the first limb other than the first area when the first limb is clamped with both the first and second clamps;

a third electrode disposed on an inner surface of the first lower clamp body and facing the first electrode, wherein, when the first limb is clamped with the first clamp electrode apparatus, the third electrode is configured to contact a third area of the first limb located at the same distance of the first area from the ulnar head or the malleolus when measured along the longitudinal direction of the first limb; and a fourth electrode disposed on an inner surface of the second lower clamp body and facing the second electrode, the fourth electrode is configured to contact a fourth area of the first limb located at the same distance of the second area from the ulnar head or the malleolus when measured along the longitudinal direction of the first limb;

a second clamp electrode apparatus comprising a fifth electrode and a sixth electrode and mountable on a second limb of the same subject;

a current source circuit;

a voltage measurement circuit;

first, second, third, fourth, fifth and sixth terminals configured to be connected to the first, second, third, fourth, fifth and sixth electrodes, respectively; and at least one switching circuit configured to connect each of the first, second, third, fourth, fifth and sixth terminals to either the current source circuit or the voltage measurement circuit, wherein the at least one switching circuit is configured to switch connection of each of the first and second terminals to the current source circuit and further configured to switch connection of each of the third and fourth terminals to the voltage measurement circuit such that:

in a first measurement, the first and fifth terminals are connected to the current source circuit and the third and sixth terminals are connected to the voltage measurement circuit, and in a second measurement immediately subsequent to the first measurement, the second and fifth terminals are connected to the current source circuit and the fourth and the sixth terminals are connected to the voltage measurement circuit while the first clamp electrode apparatus maintains clamping the first limb, wherein the at least one switching circuit is configured to connect the fifth electrode to the current source circuit and further configured to connect the sixth electrode to the voltage measurement circuit both in the first measurement and the second measurement;

clamping the first limb of the subject with the first clamp electrode apparatus:

such that the ulnar head or malleolus of the first limb is positioned within the opening or channel of the first clamp electrode apparatus while contacting both the first edge and the second edge of the first clamp electrode apparatus for the first edge and the second edge to restrict the movement of the first clamp electrode apparatus along the longitudinal direction of the first limb, such that the first electrode disposed on the inner surface of the first upper clamp body is spaced apart in the longitudinal direction of the first limb from an imaginary line that is perpendicular to the longitudinal direction of the first limb and passes the ulnar head or malleolus of the first limb;

such that the second electrode disposed on the inner surface of the second upper clamp body is spaced apart in the longitudinal direction of the first limb from the imaginary line that is perpendicular to the longitudinal direction of the first limb and passes the ulnar head or malleolus of the first limb; and further such that the first, second, third and fourth electrodes contact the first, second, third and fourth areas of the first limb;

clamping the second limb of the subject with the second clamp electrode apparatus such that an ulnar head or malleolus of the second limb is positioned within the opening or channel of the second clamp electrode apparatus while the first edge and the second edge of the second clamp electrode apparatus contact the ulnar head or malleolus of the second limb and restrict a movement of the second clamp electrode apparatus along a longitudinal direction of the second limb, and such that the fifth and sixth electrodes contact the fifth and sixth areas of the second limb;

electrically connecting the first, second, third, fourth, fifth and sixth electrodes to the first, second, third, fourth, fifth and sixth terminals, respectively;

conducting the first measurement while the first and fifth terminals are connected to the current source circuit, the third and sixth terminals are connected to the voltage measurement circuit, wherein the first measurement is made between the third electrode and the sixth electrode to acquire a first voltage drop between the third and sixth electrodes;

while maintaining clamping of the first limb with the first clamp electrode apparatus and further maintaining clamping of the second limb with the second clamp electrode apparatus, switching electrical connections of the first, second, third and fourth terminals such that the first and third terminals are disconnected from the current source circuit and the voltage measurement circuit, respectively, and the second and fourth terminals are connected to the current source circuit and the voltage measurement circuit, respectively, while maintaining the fifth terminal's connection to the current source circuit and the sixth terminal's connection to the voltage measurement circuit; and conducting the second measurement while the second and sixth terminals are connected to the current source circuit and the fourth and fifth terminals are connected to the voltage measurement circuit, wherein the second measurement is made between the fourth electrode and the sixth electrode to acquire a second voltage drop between the fourth and sixth electrodes;

unclamping the first and second limbs of the subject; and subsequently, re-clamping the first limb of the subject with the first clamp electrode apparatus such that the ulnar head or malleolus of the first limb is positioned within the opening or channel of the first clamp electrode apparatus, wherein re-clamping the first limb comprises placing the first clamp electrode apparatus such that the opening or channel of the first clamp electrode apparatus is slightly misaligned with reference to the ulnar head or malleolus of the first limb, which causes at least one of the first edge and the second edge to slide on a slanted surface of the ulnar head or malleolus of the first limb for adjusting its position and/or orientation to have the ulnar head or malleolus of the first limb positioned within the opening or channel of the first clamp electrode apparatus and further to have the first, second, third and fourth electrodes respectively contact the first, second, third and fourth areas;

re-clamping the second limb of the subject with the second clamp electrode apparatus such that the ulnar head or malleolus of the second limb is positioned within the opening or channel of the second clamp electrode apparatus;

electrically connecting the first, second, third, fourth, fifth and sixth electrodes to the first, second, third, fourth, fifth and sixth terminals, respectively;

conducting a third measurement while the first and fifth terminals are connected to the current source circuit, the third and sixth terminals are connected to the voltage measurement circuit, wherein the third measurement is made between the third electrode and the sixth electrode to acquire a third voltage drop between the third and sixth electrodes.

2. The method of claim 1, further comprising processing the first and second voltage drops to obtain a value representing impedance of a section of the first limb between the first and second electrodes.

3. The method of claim 1, further comprising calculating a value representing impedance of a body section comprising an arm, a trunk and a leg using the first and second voltage drops.

4. The method of claim 1, further comprising processing the first and second voltage drops with a formula or a lookup table to assess body composition of the subject.

5. The method of claim 1, wherein the first limb is a leg, the second limb is an arm.

6. The method of claim 1, wherein the first limb is an arm, the second limb is a leg.

7. The method of claim 1, wherein the first limb is a leg which comprises an ankle section between the first and second electrodes, wherein the method further comprises:

processing the first and second voltage drops to obtain a value representing body water amount in the ankle section; and determining if the obtained value is greater than a predetermined value; and when determined that the obtained value is greater than the predetermined value, determining that the subject has edema.

8. The method of claim 1, further comprising:

after conducting the third measurement, while maintaining clamping of the first limb with the first clamp electrode apparatus and further maintaining clamping of the second limb with the second clamp electrode apparatus, switching electrical connections of the first, second, third and fourth terminals such that the first and third terminals are disconnected from the current source circuit and the voltage measurement circuit, respectively, and the second and fourth terminals are connected to the current source circuit and the voltage measurement circuit, respectively, while maintaining the fifth terminal's connection to the current source circuit and the sixth terminal's connection to the voltage measurement circuit, and conducting a fourth measurement while the second and sixth terminals are connected to the current source circuit and the fourth and sixth terminals are connected to the voltage measurement circuit, wherein the fourth measurement is made between the fourth electrode and the sixth electrode to acquire a fourth voltage drop between the fourth and sixth electrodes.

9. The method of claim 8, further comprising processing the first, second, third and fourth voltage drops to identify changes of body composition of the subject.

10. The method of claim 8, further comprising:

processing the first, second, third and fourth voltage drops to obtain a value representing difference between water amounts in a section of the first limb at different measuring times;

determining if the obtained value is greater than a predetermined value; and when determined that the obtained value is greater than the predetermined value, determining that the subject has edema.

* * * * *